(12) United States Patent
Holdcroft et al.

(10) Patent No.: US 10,800,874 B2
(45) Date of Patent: Oct. 13, 2020

(54) POLY(PHENYLENE) AND M-TERPHENYL AS PROTECTING GROUPS FOR BENZIMIDAZOLIUM HYDROXIDES

(71) Applicant: Simon Fraser University, Burnaby (CA)

(72) Inventors: Steven Holdcroft, Pitt Meadows (CA); Andrew Wright, Burnaby (CA)

(73) Assignee: Simon Fraser University, Burnaby (CA)

( * ) Notice: Subject to any disclaimer, the term of this patent is extended or adjusted under 35 U.S.C. 154(b) by 89 days.

(21) Appl. No.: 16/068,654

(22) PCT Filed: Jan. 6, 2017

(86) PCT No.: PCT/CA2017/050013
§ 371 (c)(1),
(2) Date: Jul. 6, 2018

(87) PCT Pub. No.: WO2017/117678
PCT Pub. Date: Jul. 13, 2017

(65) Prior Publication Data
US 2019/0016851 A1 Jan. 17, 2019

Related U.S. Application Data

(60) Provisional application No. 62/276,724, filed on Jan. 8, 2016.

(51) Int. Cl.
| C08G 61/00 | (2006.01) |
| C08G 61/10 | (2006.01) |
| C07D 235/18 | (2006.01) |
| B01D 67/00 | (2006.01) |
| B01D 71/28 | (2006.01) |
| C08J 5/22 | (2006.01) |
| C25B 11/04 | (2006.01) |
| H01M 4/86 | (2006.01) |
| C25B 13/08 | (2006.01) |

(52) U.S. Cl.
CPC ......... *C08G 61/10* (2013.01); *B01D 67/0009* (2013.01); *B01D 71/28* (2013.01); *C07D 235/18* (2013.01); *C08J 5/2256* (2013.01); *C25B 11/0489* (2013.01); *C25B 13/08* (2013.01); *H01M 4/8663* (2013.01); *B01D 2325/14* (2013.01); *C08G 2261/149* (2013.01); *C08G 2261/312* (2013.01); *C08G 2261/614* (2013.01); *C08G 2261/62* (2013.01); *C08J 2365/02* (2013.01); *Y02P 20/55* (2015.11)

(58) Field of Classification Search
CPC ...... C08G 6/10; C08G 61/10; C08G 2261/49; C08G 2261/614; C08G 73/19; B01D 67/009; B01D 71/28; C08J 5/2256; C08J 2365/02; C08J 3/24; C07D 235/18; C07D 233/64; C25B 11/0489; C25B 13/08; C25B 1/10; C25B 9/10; H01M 4/8663; H01M 4/926; H01M 4/96; A61P 31/00
USPC .......................................................... 521/27
See application file for complete search history.

(56) References Cited

U.S. PATENT DOCUMENTS

| 3,255,078 | A | 6/1966 | Heinroth et al. |
| 7,301,002 | B1 | 11/2007 | Cornelius et al. |
| 8,110,636 | B1 | 2/2012 | Fujimoto et al. |
| 9,315,630 | B2 * | 4/2016 | Thomas ................. C08G 73/18 |
| 9,509,008 | B2 | 11/2016 | Kim et al. |
| 9,511,362 | B2 * | 12/2016 | Thomas ................. C08G 73/18 |
| 10,005,886 | B2 * | 6/2018 | Holdcroft ............. C08J 5/2256 |
| 2003/0099838 | A1 | 5/2003 | Cho et al. |
| 2009/0026544 | A1 | 1/2009 | Uno et al. |
| 2012/0186446 | A1 | 7/2012 | Bara et al. |
| 2012/0256296 | A1 | 10/2012 | Wei et al. |
| 2019/0169372 | A1 * | 6/2019 | Holdcroft .................. C08J 3/24 |
| 2019/0202991 | A1 * | 7/2019 | Holdcroft ............... H01M 4/90 |
| 2019/0382353 | A1 * | 12/2019 | Holdcroft ............... A61P 31/00 |

FOREIGN PATENT DOCUMENTS

| CA | 2866742 A1 | 10/2013 |
| CA | 2933312 A1 | 9/2016 |
| JP | 2009-087687 A | 4/2009 |
| JP | 2012-128142 A | 7/2012 |
| KR | 2012115848 A1 | 10/2012 |
| KR | 20120115848 A | 10/2012 |
| WO | 2009/134227 A1 | 11/2009 |
| WO | 2013/149328 A1 | 10/2013 |
| WO | 2014/012188 A1 | 1/2014 |
| WO | 2015/157848 A1 | 10/2015 |

(Continued)

OTHER PUBLICATIONS

Extended European Search Report dated Sep. 4, 2019, issued in corresponding European Application No. EP 17735788.6, filed Jan. 6, 2017, 6 pages.

(Continued)

*Primary Examiner* — Hannah J Pak
(74) *Attorney, Agent, or Firm* — Christensen O'Connor Johnson Kindness PLLC

(57) ABSTRACT

The present disclosure provides alkaline-stable m-terphenyl benzimidazolium hydroxide compounds, in which the C2-position is attached to a phenyl group having various substituents at the ortho positions. Polymers incorporating m-terphenylene repeating groups derived from these alkaline-stable benzimidazolium hydroxide compounds are also presented, along with their inclusion in ionic membranes and in electrochemical devices.

10 Claims, 16 Drawing Sheets

(56) References Cited

FOREIGN PATENT DOCUMENTS

| WO | 2015153959 A1 | 10/2015 |
| WO | 2015153959 A2 | 10/2015 |

OTHER PUBLICATIONS

Richter, D., et al., "Kinetics of Hydride Abstractions from 2-Arylbenzimidazolines," Chemistry—An Asian Journal vol. 4: 1824-1829, 2009.
Williams, T., et al., "Mechanistic Elucidatin of the Arylation of Non-Spectator N-Heterocyclic Carbenes at Copper Using a Combined Experimental and Computational Approach," Organometallics 34(14): 3497-3507, Jul. 2015.
Wright, A.G., et al., "Poly(phenylene) and m-Terphenyl as Powerful Protecting Groups for the Preparation of Stable Organic Hydroxides," Angewandte Chemie, International Edition 55(15): 4818-4821, Mar. 2016.
Zimmermann, T., et al., "Ring Transformations of Heterocyclic Compounds XIV [1]. Ring Transformations of Pyrylium and Thiopyrylium Salts with Anhydro-bases Derived from 1H-Benzimidazolium and Benzothiazolium Salts: An Easy Access to 2-(2,4,6-Triarylphenyl) 1H-Benzimidazolium and Benzothiazolium Derivatives" J. Heterocycl Chem., 33(6): 1717-1721, 1996.
Zhu, X-Q., et al., "Hydride, Hydrogen atom, Proton and Electron Transfer Driving Forces of various Five-membered Heterocyclic Organic Hydrides and their Reaction Intermediates in Acetonitrile" J. Med. Chem. Soc. vol. 130: 2501-2516, 2008.
Extended European Search Report dated Sep. 6, 2017, issued in European Application No. 15780051.7, filed Apr. 15, 2015, 5 pages.
Fan, J., et al., "Cationic Polyelectrolytes, Stable in 10 M KOHaq at 100° C.," Macro Letters 6(10):1089-1093, Sep. 2017.
Henkensmeier et al., "Polybenzimidazolium-Based Solid Electrolytes", Macromolecular Materials and Engineering, Jul. 22, 2011, vol. 296, p. 899-908; p. 900, left col, para 3, p. 905, Scheme 3, p. 908, left col, para 1.
International Search Report and Written Opinion dated Dec. 21, 2017, issued in corresponding International Application No. PCT/US2017/44772, filed Aug. 1, 2017, 11 pages.
International Search Report and Written Opinion dated Jul. 16, 2013, issued in corresponding International Application No. PCT/CA2013/000323, filed Apr. 4, 2013, 8 pages.
International Search Report and Written Opinion dated Oct. 18, 2017, issued in corresponding International Application No. PCT/US2017/44554, filed Jul. 29, 2017, 7 pages.
International Search Report dated Jul. 8, 2015, issued in corresponding International Application No. PCT/CA2015/000248, filed Apr. 15, 2015, 8 pages.
International Search Report dated Mar. 17, 2017, issued in corresponding International Application No. PCT/CA2017/050013, filed Jan. 6, 2017, 5 pages.
Long, H., and B. Pivovar, "Hydroxide Degradation Pathways for Imidazolium Cations: A DFT Study," Journal of Physical Chemistry 118(19):9880-9888, Apr. 2014.
Pu, H., et al., "Synthesis and Characterization of Fluorine-Containing Polybenzimidazole for Proton Conducting Membranes in Fuel Cells," Journal of Polymer Science: Part A: Polymer Chemistry 48:2115-2122, 2010.
Takagi, K., et al., "Synthesis of Imidazole-Containing Conjugated Polymers Bearing Phenol Unit as Side Group and Excited State Intramolecular Proton Transfer-Mediated Fluorescence," Journal of Polymer Science: Part A: Polymer Chemistry 47:4822-4829, 2009.
Weissbach et al., "Simultaneous, Synergistic Control of Ion Exchange Capacity and Cross-Linking of Sterically-Protected Poly(benzimidazolium)s" Chemistry of Materials, Oct. 19, 2016, vol. 28, p. 8060-8070; entire document.

Wright, A.G., et al., "Hexamethyl-p-terphenyl poly(benzimidazolium): A Universal Hydroxide-Conducting Polymer for Energy Conversion Devices," Energy & Environmental Science 9(6):2130-2142, May 2016.
Wright, A.G., and S. Holdcroft, "Hydroxide-Stable Ionenes," ACS Macro Letters 3:444-447, 2014.
Sun, Q., et al. "Synthesis and Biological Evaluation of Analogues of AKT (Protein Kinase B) inhibitor-IV," J. Med. Chem., vol. 54, pp. 1126-1139, 2011.
International Search Report, dated Mar. 8, 2017 in related International Application No. PCT/CA2017/050013, filed Jan. 6, 2017, 5 pages.
Written Opinion of the International Searching Authority, dated Mar. 8, 2017 in related International Application No. PCT/CA2017/050013, filed Jan. 6, 2017, 6 pages.
Williams, T., et al. "Mechanistic Elucidation of the Arylation of Non-Spectator N-Heterocyclic Carbenes at Copper Using a Combined Experimental and Computational Approach," Organometallics, vol. 34, No. 14, pp. 3497-3507, 2015.
Zhu, X. Q., et al. "Hydride, Hydrogen atom, Proton and Electron Transfer Driving Forces of various Five-membered Heterocyclic Organic Hydrides and their Reaction Intermediates in Acetonitrile," J. Am. Chem. Soc., vol. 130, pp. 2501-2516, 2008.
Zimmermann, T. et al. "Ring Transformations of Heterocyclic Compounds. XIV [1]. Ring Transformations of Pyrylium and Thiopyrylium Salts with Anhydro-bases Derived from 1H-Benzimidazolium and Benzothiazolium Salts: An Easy Access to 2-(2, 4, 6-Triarylphenyl) 1H-Benzimidazolium and Benzothiazolium Derivatives," J. Heterocyclic Chem., vol. 33, pp. 1717-1721, Nov.-Dec. 1996.
Xing, B., et al., "Hydrogen/Oxygen Polymer Electrolyte Membrane Fuel Cells (PEMFCs) Based on Alkaline-Doped Polybenzimidazole (PBI)," Electrochem. Comm., 2(10), 697-702, 2000.
Hou, H., et al., "Alkali Doped Polybenzimidazole Membrane for Alkaline Direct Methanol Fuel Cell," In. J. Hydrogen Energy, 33(23), 7172-7176, 2008.
Novitski, D., et al., "Electrochemical Reduction of Dissolved Oxygen in Alkaline, Solid Polymer Electrolyte Films," J. Am. Chem. Soc., 138, 15465-15472, Nov. 2, 2016.
Thomas, O. D., et al., "A Stable Hydroxide-Conducting Polymer," J. Am. Chem. Soc., 134 (26), 10753-10756, 2012.
Thomas, O. D., et al., "Anion Conducting Poly(Dialkyl Benzimidazolium) Salts," Poly. Chem., 2, 1641-1643, 2011.
International Search Report and Written Opinion dated Jun. 13, 2018, issued in corresponding International Application No. PCT/CA2018/050436, filed Apr. 10, 2018, 10 pages.
Skalski, J., et al., Structurally-Defined, Sulfo-Phenylated, Oligophenylenes and Polyphenylenes, J. Am. Chem. Soc., 137, 12223-12226, 2015.
Adamski, M., et al., "Highly Stable, Low Gas Grossover, Proton-Conducting Phenylated Polyphenylenes," Angew. Chem. Int. Ed., 56, 9058-9061, 2017.
Lim, Y., et al., "Synthesis and Properties of Sulfonated Poly(Phyenylene Sulfone)s Without Ether Linkage by Diels-Alder Reaction for PEMFC Application," Electrochimica Acta 119, 16-23, 2014.
Partial International Search Report as dated Feb. 26, 2020, issued in corresponding European Application No. 17837493.0, filed Aug. 1, 2017, 14 pages.
Valtcheva, I.B., et al., "Crosslinked Polybenzimidazole Membranes for Organic Solvent NanoFiltration (OSN): Analysis of Crosslinking Reaction Mechanism and Effects of Reaction Parameters," Journal of Membrane Science 493, Mar. 2015, 568-579.
Written Opinion dated Mar. 8, 2017, issued in corresponding International Application No. PCT/CA2017/050013, filed Jan. 6, 2017, 6 pages.
European Search Report dated Oct. 31, 2019, issued in corresponding European Application No. 17792325.7, filed May 1, 2017, 10 pages.

* cited by examiner

POLY(PHENYLENE) AND M-TERPHENYL AS PROTECTING GROUPS FOR BENZIMIDAZOLIUM HYDROXIDES

CROSS-REFERENCE TO RELATED APPLICATION

This application claims the benefit of U.S. Provisional Application No. 62/276,724, filed Jan. 8, 2016, the disclosure of which is incorporated herein by reference in its entirety.

BACKGROUND

Immobilized quaternary ammoniums are a class of cationic head groups that support the conduction of anions. They have been used in a range of technologies, such as anion-exchange resins, hydrogen fuel cells, water electrolyzers, redox-flow batteries, and reverse dialysis. However, of the numerous reported cationic groups, few show promise of long term stability under strong alkaline conditions at elevated temperatures (e.g., 80° C.). A sub-class of cationic head group that are attracting increasing attention are sterically-protected imidazoliums and benzimidazoliums.

There is a need for alkaline-stable cationic head groups that can be used in anion-exchange resins, hydrogen fuel cells, and the like. The present disclosure seeks to fulfill these needs and provides further related advantages.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, the present disclosure features a compound of Formula (I):

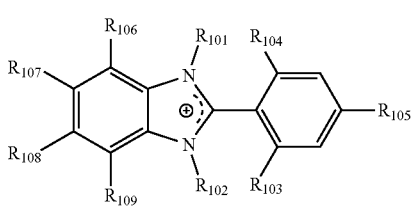

(I)

wherein $R_{101}$ and $R_{102}$ are each independently selected from alkyl, perfluoroalkyl, heteroalkyl, aryl, aralkyl, and heteroaryl;

$R_{103}$ and $R_{104}$ are each independently selected from hydrogen, alkyl, perfluoroalkyl, heteroalkyl, aryl, aralkyl, heteroaryl, and halo, wherein said alkyl, perfluoroalkyl, heteroalkyl, aryl, aralkyl, or heteroaryl is each optionally substituted with 1, 2, 3, or 4 substituents independently selected from alkyl and halo;

$R_{105}$ is selected from hydrogen, alkyl, perfluoroalkyl, heteroalkyl, aryl, aralkyl, and heteroaryl;

$R_{106}$, $R_{107}$, $R_{108}$, and $R_{109}$ are independently selected from hydrogen, alkyl, perfluoroalkyl, heteroalkyl, aryl, aralkyl, and heteroaryl.

In another aspect, the present disclosure features a polymer including a repeating unit derived from a compound of Formula (I).

In yet another aspect, the present disclosure features a polymer including repeating units of Formula (II-A) and (II-B):

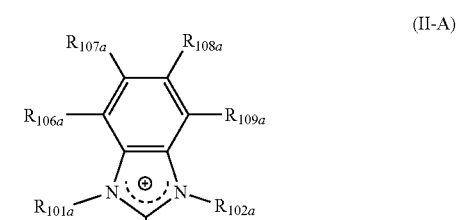

(II-A)

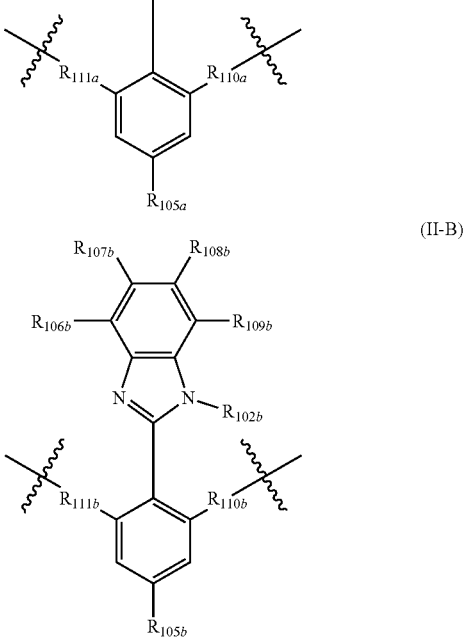

(II-B)

wherein:

$R_{101a}$, $R_{102a}$, and $R_{102b}$ are each independently selected from alkyl, perfluoroalkyl, heteroalkyl, aryl, aralkyl, and heteroaryl;

$R_{111a}$, $R_{110a}$, $R_{111b}$, and $R_{110b}$ are each independently selected from alkylene, perfluoroalkylene, heteroalkylene, arylene, aralkylene, heteroarylene, wherein said alkylene, perfluoroalkylene, heteroalkylene, arylene, aralkylene, or heteroarylene is each optionally substituted with 1, 2, 3, or 4 substituents independently selected from alkyl and halo;

$R_{105a}$ and $R_{105b}$ are each independently selected from hydrogen, alkyl, perfluoroalkyl, heteroalkyl, aryl, aralkyl, and heteroaryl;

$R_{106a}$, $R_{107a}$, $R_{108a}$, $R_{109a}$, $R_{106b}$, $R_{107b}$, $R_{108b}$, and $R_{109b}$ are each independently selected from hydrogen, alkyl, perfluoroalkyl, heteroalkyl, aryl, aralkyl, and heteroaryl, wherein the polymer comprises comprising r mole percentage repeating units of Formula (II-A), and s mole percentage repeating units of Formula (II-B), and r is from 1 mole percent to 100 mole percent, s is from 0 mole percent to 99 mole percent, and r+s=100%.

In yet a further aspect, the present disclosure features an ionic membrane including a polymer including repeating units of Formula (II-A) and/or (II-B).

In yet a further aspect, the present disclosure features a polymer including repeating units of Formula (II-A) and/or (II-B), incorporated into a catalyst layer of a fuel cell, of an electrolyzer, or of other electrochemical devices.

DESCRIPTION OF THE DRAWINGS

The foregoing aspects and many of the attendant advantages of this disclosure will become more readily appreciated as the same become better understood by reference to the following detailed description, when taken in conjunction with the accompanying drawings, wherein.

DETAILED DESCRIPTION

Figure 1A:
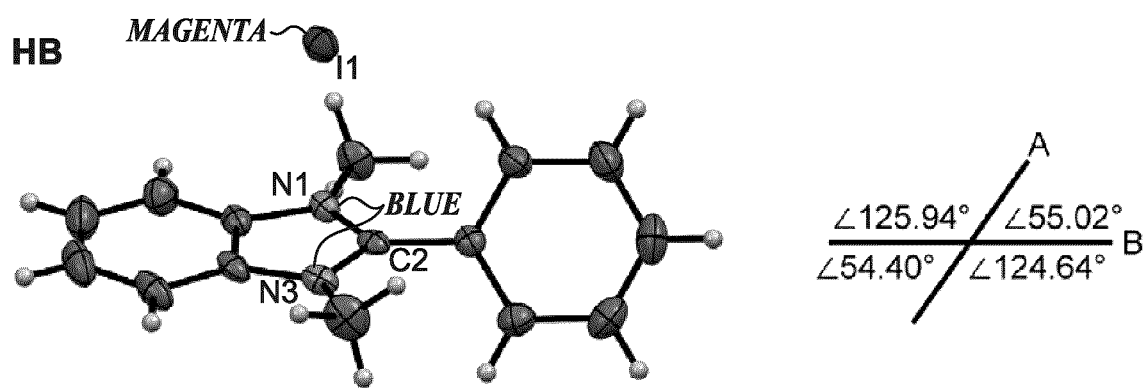
FIGS. 1A-1D show X-ray crystal structures of embodiments of model compounds in their iodide form with thermal ellipsoids at a 50% probability level alongside the dihedral angles measured (A represents the 2-phenyl plane and B represents the benzimidazolium plane). Only one of the two unique BrB structures is shown for clarity and PhB co-crystallized with $H_2O$ (where the hydrogens of $H_2O$ are not shown).
Figure 1B:
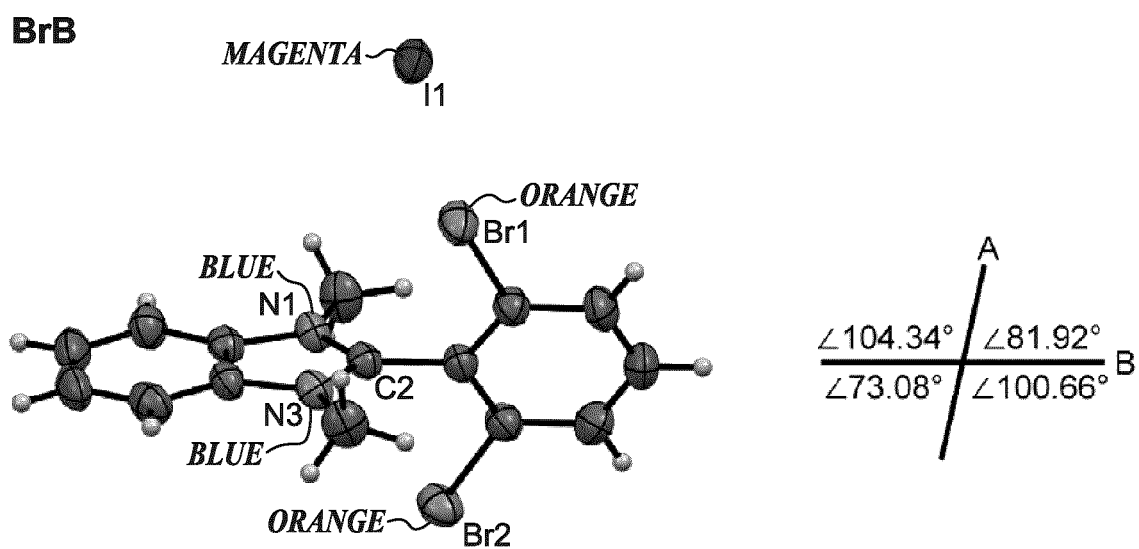
Figure 1C:
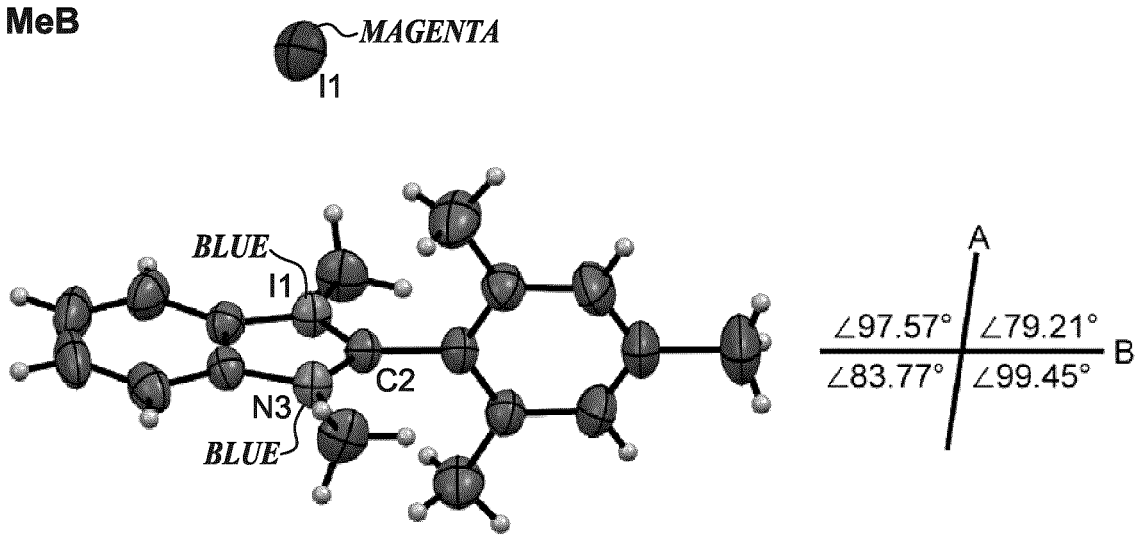
Figure 1D:
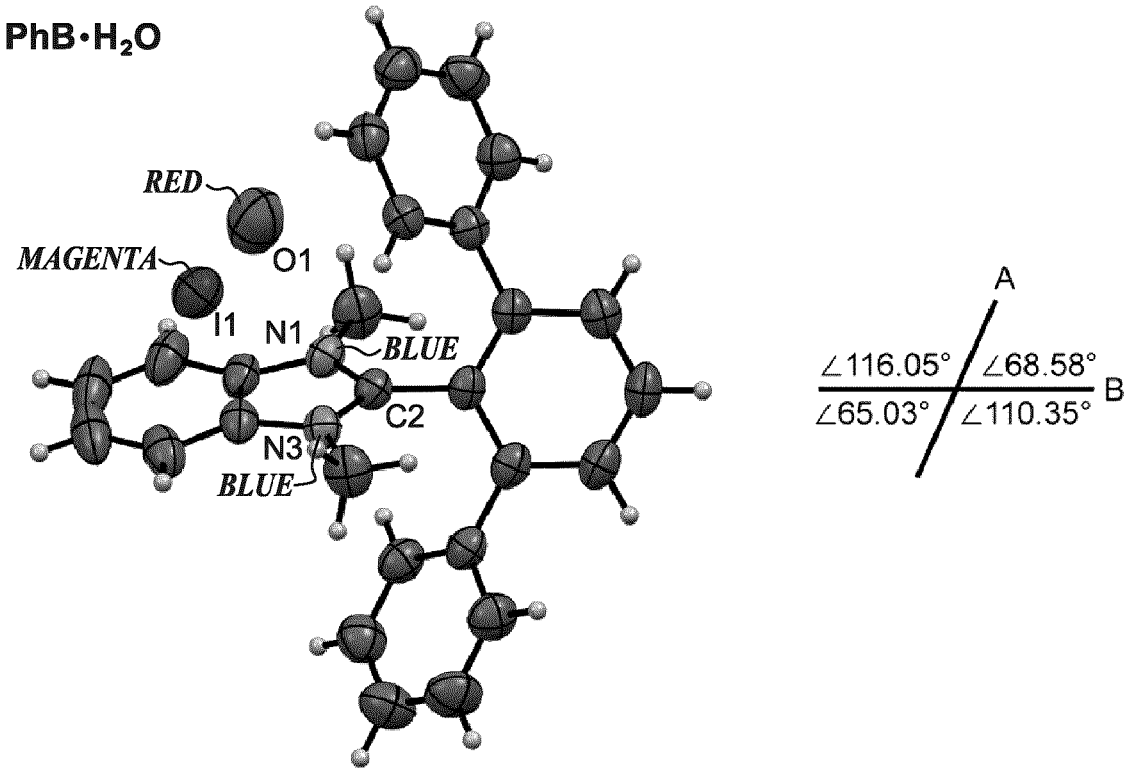

The present disclosure provides alkaline-stable benzimidazolium hydroxide compounds, in which the C2-position is attached to a phenyl group having various substituents at the ortho positions. Polymers incorporating repeating groups derived from the alkaline-stable compounds of the present disclosure are also presented.

Definitions

At various places in the present specification, substituents of compounds of the disclosure are disclosed in groups or in ranges. It is specifically intended that the disclosure include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

It is further intended that the compounds of the disclosure are stable. As used herein "stable" refers to a compound that is sufficiently robust to survive isolation to a useful degree of purity from a reaction mixture.

It is further appreciated that certain features of the disclosure, which are, for clarity, described in the context of separate embodiments, can also be provided in combination in a single embodiment. Conversely, various features of the disclosure which are, for brevity, described in the context of a single embodiment, can also be provided separately or in any suitable subcombination.

"Optionally substituted" groups can refer to, for example, functional groups that may be substituted or unsubstituted by additional functional groups. For example, when a group is unsubstituted, it can be referred to as the group name, for example alkyl or aryl. When a group is substituted with additional functional groups, it may more generically be referred to as substituted alkyl or substituted aryl.

As used herein, the term "substituted" or "substitution" refers to the replacing of a hydrogen atom with a substituent other than H. For example, an "N-substituted piperidin-4-yl" refers to replacement of the H atom from the NH of the piperidinyl with a non-hydrogen substituent such as, for example, alkyl.

As used herein, the term "alkyl" refers to a straight or branched hydrocarbon groups. In some embodiments, alkyl has 1 to 10 carbon atoms (e.g., 1 to 8 carbon atoms, 1 to 6 carbon atoms, 1 to 3 carbon atoms, 1 or 2 carbon atoms, or 1 carbon atom). Representative alkyl groups include methyl, ethyl, propyl (e.g., n-propyl, isopropyl), butyl (e.g., n-butyl, sec-butyl, and tert-butyl), pentyl (e.g., n-pentyl, tert-pentyl, neopentyl, isopentyl, pentan-2-yl, pentan-3-yl), and hexyl (e.g., n-hexyl and isomers) groups.

As used herein, the term "alkylene" refers to a linking alkyl group.

As used herein, the term "cycloalkyl" refers to non-aromatic carbocycles including cyclized alkyl, alkenyl, and alkynyl groups. Cycloalkyl groups can include mono- or polycyclic (e.g., having 2, 3 or 4 fused rings) ring systems, including spirocycles. In some embodiments, cycloalkyl groups can have from 3 to about 20 carbon atoms, 3 to about 14 carbon atoms, 3 to about 10 carbon atoms, or 3 to 7 carbon atoms. Cycloalkyl groups can further have 0, 1, 2, or 3 double bonds and/or 0, 1, or 2 triple bonds. Also included in the definition of cycloalkyl are moieties that have one or more aromatic rings fused (i.e., having a bond in common with) to the cycloalkyl ring, for example, benzo derivatives of pentane, pentene, hexane, and the like. A cycloalkyl group having one or more fused aromatic rings can be attached though either the aromatic or non-aromatic portion. One or more ring-forming carbon atoms of a cycloalkyl group can be oxidized, for example, having an oxo or sulfido substituent. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcamyl, adamantyl, and the like.

As used herein, the term "cycloalkylene" refers to a linking cycloalkyl group.

As used herein, the term "perfluoroalkyl" refers to straight or branched fluorocarbon chains. In some embodiments, perfluoroalkyl has 1 to 10 carbon atoms (e.g., 1 to 8 carbon atoms, 1 to 6 carbon atoms, 1 to 3 carbon atoms, 1 or 2 carbon atoms, or 1 carbon atom). Representative alkyl groups include trifluoromethyl, pentafluoroethyl, etc.

As used herein, the term "perfluoroalkylene" refers to a linking perfluoroalkyl group.

As used herein, the term "heteroalkyl" refers to a straight or branched chain alkyl groups and where one or more of the carbon atoms is replaced with a heteroatom selected from O, N, or S. In some embodiments, heteroalkyl alkyl has 1 to 10 carbon atoms (e.g., 1 to 8 carbon atoms, 1 to 6 carbon atoms, 1 to 3 carbon atoms, 1 or 2 carbon atoms, or 1 carbon atom).

As used herein, the term "heteroalkylene" refers to a linking heteroalkyl group.

As used herein, the term "alkoxy" refers to an alkyl or cycloalkyl group as described herein bonded to an oxygen atom. In some embodiments, alkoxy has 1 to 10 carbon atoms (e.g., 1 to 8 carbon atoms, 1 to 6 carbon atoms, 1 to 3 carbon atoms, 1 or 2 carbon atoms, or 1 carbon atom). Representative alkoxy groups include methoxy, ethoxy, propoxy, and isopropoxy groups.

As used herein, the term "perfluoroalkoxy" refers to a perfluoroalkyl or cyclic perfluoroalkyl group as described herein bonded to an oxygen atom. In some embodiments, perfluoroalkoxy has 1 to 10 carbon atoms (e.g., 1 to 8 carbon atoms, 1 to 6 carbon atoms, 1 to 3 carbon atoms, 1 or 2 carbon atoms, or 1 carbon atom). Representative perfluoroalkoxy groups include trifluoromethoxy, pentafluoroethoxy, etc.

As used herein, the term "aryl" refers to an aromatic hydrocarbon group having 6 to 10 carbon atoms. Representative aryl groups include phenyl groups. In some embodiments, the term "aryl" includes monocyclic or polycyclic (e.g., having 2, 3, or 4 fused rings) aromatic hydrocarbons such as, for example, phenyl, naphthyl, anthracenyl, phenanthrenyl, indanyl, and indenyl.

As used herein, the term "arylene" refers to a linking aryl group. For example, the term "phenylene" refers to a linking phenyl group.

As used herein, the term "aralkyl" refers to an alkyl or cycloalkyl group as defined herein with an aryl group as defined herein substituted for one of the alkyl hydrogen atoms. A representative aralkyl group is a benzyl group.

As used herein, the term "aralkylene" refers to a linking aralkyl group.

As used herein, the term "heteroaryl" refers to a 5- to 10-membered aromatic monocyclic or bicyclic ring containing 1-4 heteroatoms selected from O, S, and N. Representative 5- or 6-membered aromatic monocyclic ring groups include pyridine, pyrimidine, pyridazine, furan, thiophene, thiazole, oxazole, and isooxazole. Representative 9- or 10-membered aromatic bicyclic ring groups include benzofuran, benzothiophene, indole, pyranopyrrole, benzopyran, quionoline, benzocyclohexyl, and naphthyridine.

As used herein, the term "heteroarylene" refers to a linking heteroaryl group.

As used herein, the term "halogen" or "halo" refers to fluoro, chloro, bromo, and iodo groups.

As used herein, when a benzimidazolium or an imidazolium is positively charged, for example, as illustrated below for an imidazolium,

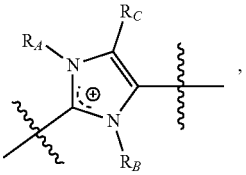

it is understood that the illustrated structure encompasses a double bond that may be located in one of two positions and the positive charge is consequently localized on one of the two ring-forming nitrogen atoms:

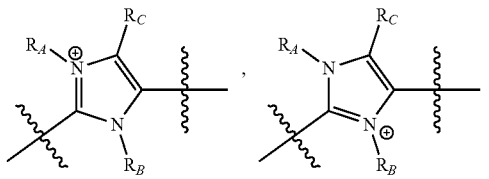

As used herein, the term "copolymer" refers to a polymer that is the result of polymerization of two or more different monomers. The number and the nature of each constitutional unit can be separately controlled in a copolymer. The constitutional units can be disposed in a purely random, an alternating random, a regular alternating, a regular block, or a random block configuration unless expressly stated to be otherwise. A purely random configuration can, for example, be: x-x-y-z-x-y-y-z-y-z-z-z . . . or y-z-x-y-z-y-z-x-x . . . . An alternating random configuration can be: x-y-x-z-y-x-y-z-y-x-z . . . , and a regular alternating configuration can be: x-y-z-x-y-z-x-y-z . . . . A regular block configuration (i.e., a block copolymer) has the following general configuration: . . . x-x-x-y-y-y-z-z-z-x-x-x . . . , while a random block configuration has the general configuration: . . . x-x-x-z-z-x-x-y-y-y-z-z-z-x-x-z-z-z- . . . .

As used herein, the term "random copolymer" is a copolymer having an uncontrolled mixture of two or more constitutional units. The distribution of the constitutional units throughout a polymer backbone (or main chain) can be a statistical distribution, or approach a statistical distribution, of the constitutional units. In some embodiments, the distribution of one or more of the constitutional units is favored.

As used herein, the term "constitutional unit" of a polymer refers to an atom or group of atoms in a polymer, comprising a part of the chain together with its pendant atoms or groups of atoms, if any. The constitutional unit can refer to a repeating unit. The constitutional unit can also refer to an end group on a polymer chain. For example, the constitutional unit of polyethylene glycol can be —CH$_2$CH$_2$O— corresponding to a repeating unit, or —CH$_2$CH$_2$OH corresponding to an end group.

As used herein, the term "repeating unit" corresponds to the smallest constitutional unit, the repetition of which constitutes a regular macromolecule (or oligomer molecule or block).

As used herein, the term "end group" refers to a constitutional unit with only one attachment to a polymer chain, located at the end of a polymer. For example, the end group can be derived from a monomer unit at the end of the polymer, once the monomer unit has been polymerized. As another example, the end group can be a part of a chain transfer agent or initiating agent that was used to synthesize the polymer.

As used herein, the term "terminus" of a polymer refers to a constitutional unit of the polymer that is positioned at the end of a polymer backbone.

As used herein, the term "cationic" refers to a moiety that is positively charged, or ionizable to a positively charged moiety under physiological conditions. Examples of cationic moieties include, for example, amino, ammonium, pyridinium, imino, sulfonium, quaternary phosphonium groups, etc.

As used herein, the term "anionic" refers to a functional group that is negatively charged, or ionizable to a negatively charged moiety under physiological conditions. Examples of anionic groups include carboxylate, sulfate, sulfonate, phosphate, etc.

As used herein, the term "crosslinking moiety" refers to moieties that contain at least two reactive groups that are covalently bound to two repeating units on a given polymer or on two different polymers.

Unless otherwise defined, all technical and scientific terms used herein have the same meaning as commonly understood by one of ordinary skill in the art. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Compound and Polymer Structure

This disclosure provides, inter alia, a compound of Formula (I):

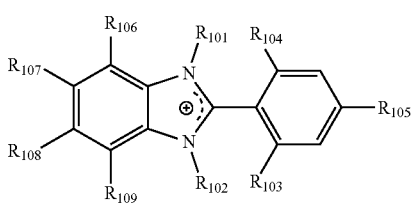

(I)

wherein $R_{101}$ and $R_{102}$ are each independently selected from alkyl, perfluoroalkyl, heteroalkyl, aryl, aralkyl, and heteroaryl;

$R_{103}$ and $R_{104}$ are each independently selected from hydrogen, alkyl, perfluoroalkyl, heteroalkyl, aryl, aralkyl, heteroaryl, and halo, wherein said alkyl, perfluoroalkyl, heteroalkyl, aryl, aralkyl, or heteroaryl is each optionally substituted with 1, 2, 3, or 4 substituents independently selected from alkyl and halo;

$R_{105}$ is selected from hydrogen, alkyl, perfluoroalkyl, heteroalkyl, aryl, aralkyl, and heteroaryl;

$R_{106}$, $R_{107}$, $R_{108}$, and $R_{109}$ are independently selected from hydrogen, alkyl, perfluoroalkyl, heteroalkyl, aryl, aralkyl, and heteroaryl.

The compounds of the present disclosure are alkaline-stable, in that less than 6 percent of a given compound degrades when exposed to an aqueous solution of 2M hydroxide at 80° C. for 170 hours. In some embodiments, the degradation is a ring opening degradation of a benzimidazolium moiety (see, e.g., Scheme 2, below). In some embodiments, the degradation includes a de-methylation of a benzimidazolium moiety (see, e.g., Scheme 2, below).

In some embodiments, $R_{101}$ and $R_{102}$ are each independently selected from $C_{1-10}$ alkyl, $C_{1-10}$ perfluoroalkyl, $C_{1-10}$ heteroalkyl, $C_{6-10}$ aryl, $C_{7-16}$ aralkyl, and $C_{5-10}$ heteroaryl.

In some embodiments, $R_{101}$ and $R_{102}$ are each independently selected from $C_{1-6}$ alkyl, $C_{1-6}$ perfluoroalkyl, $C_{1-6}$ heteroalkyl, $C_{6-10}$ aryl, $C_{7-16}$ aralkyl, and $C_{5-10}$ heteroaryl.

In some embodiments, $R_{101}$ and $R_{102}$ are each independently selected from alkyl, perfluoroalkyl, and heteroalkyl.

In some embodiments, $R_{101}$ and $R_{102}$ are each independently selected from alkyl and perfluoroalkyl.

In some embodiments, $R_{101}$ and $R_{102}$ are each independently alkyl.

In some embodiments, $R_{101}$ and $R_{102}$ are each independently selected from methyl and ethyl.

In some embodiments, $R_{101}$ and $R_{102}$ are each methyl.

In some embodiments, $R_{103}$ and $R_{104}$ are each independently selected from hydrogen, $C_{1-10}$ alkyl, $C_{1-10}$ perfluoroalkyl, $C_{1-10}$ heteroalkyl, $C_{6-10}$ aryl, $C_{7-16}$ aralkyl, $C_{5-10}$ heteroaryl, and halo, wherein said $C_{1-10}$ alkyl, $C_{1-10}$ perfluoroalkyl, $C_{1-10}$ heteroalkyl, $C_{6-10}$ aryl, $C_{7-16}$ aralkyl, or $C_{5-10}$ heteroaryl is each optionally substituted with 1, 2, 3, or 4 substituents independently selected from alkyl and halo.

In some embodiments, $R_{103}$ and $R_{104}$ are each independently selected from hydrogen, $C_{1-6}$ alkyl, $C_{1-6}$ perfluoroalkyl, $C_{1-6}$ heteroalkyl, $C_{6-10}$ aryl, $C_{7-16}$ aralkyl, $C_{5-10}$ heteroaryl, and halo, wherein said $C_{1-6}$ alkyl, $C_{1-6}$ perfluoroalkyl, $C_{1-6}$ heteroalkyl, $C_{6-10}$ aryl, $C_{7-16}$ aralkyl, or $C_{5-10}$ heteroaryl is each optionally substituted with 1, 2, 3, or 4 substituents independently selected from alkyl and halo.

In some embodiments, $R_{103}$ and $R_{104}$ are each independently selected from alkyl, perfluoroalkyl, heteroalkyl, aryl, heteroaryl, and halo, wherein said alkyl, perfluoroalkyl, heteroalkyl, aryl, or heteroaryl is each optionally substituted with 1, 2, 3, or 4 substituents independently selected from alkyl and halo.

In some embodiments, $R_{103}$ and $R_{104}$ are each independently selected from alkyl, perfluoroalkyl, heteroalkyl, aryl, heteroaryl, and halo, wherein said alkyl, perfluoroalkyl, heteroalkyl, aryl, or heteroaryl is each optionally substituted with 1, 2, 3, or 4 substituents independently selected from alkyl and halo.

In some embodiments, $R_{103}$ and $R_{104}$ are each independently selected from alkyl, perfluoroalkyl, aryl, and halo, wherein said alkyl, perfluoroalkyl, or aryl is each optionally substituted with 1, 2, 3, or 4 substituents independently selected from alkyl and halo.

In some embodiments, $R_{103}$ and $R_{104}$ are each independently selected from alkyl, aryl, and halo, wherein said alkyl or aryl is each optionally substituted with 1, 2, 3, or 4 substituents independently selected from alkyl and halo.

In some embodiments, $R_{103}$ and $R_{104}$ are each independently selected from alkyl and aryl, wherein said alkyl or aryl is each optionally substituted with 1, 2, 3, or 4 substituents independently selected from alkyl and halo.

In some embodiments, $R_{103}$ and $R_{104}$ are each independently selected from methyl and phenyl, wherein said phenyl is optionally substituted with 1, 2, 3, or 4 halo.

In some embodiments, $R_{105}$ is selected from hydrogen, $C_{1-10}$ alkyl, $C_1$-10 perfluoroalkyl, $C_{1-10}$ heteroalkyl, $C_{6-10}$ aryl, $C_{7-16}$ aralkyl, and $C_{5-10}$ heteroaryl.

In some embodiments, $R_{105}$ is selected from hydrogen, $C_{1-6}$ alkyl, $C_{1-6}$ perfluoroalkyl, $C_{1-6}$ heteroalkyl, $C_{6-10}$ aryl, $C_{7-16}$ aralkyl, and $C_{5-10}$ heteroaryl.

In some embodiments, $R_{105}$ is selected from hydrogen, alkyl, perfluoroalkyl, heteroalkyl, aryl, and heteroaryl.

In some embodiments, $R_{105}$ is selected from hydrogen, alkyl, aryl, and heteroaryl.

In some embodiments, $R_{105}$ is selected from hydrogen and alkyl.

In some embodiments, $R_{105}$ is selected from hydrogen and methyl.

In some embodiments, $R_{106}$, $R_{107}$, $R_{108}$, and $R_{109}$ are independently selected from hydrogen, $C_{1-10}$ alkyl, $C_{1-10}$ perfluoroalkyl, $C_{1-10}$ heteroalkyl, $C_{6-10}$ aryl, $C_{7-16}$ aralkyl, and $C_{5-10}$ heteroaryl.

In some embodiments, $R_{106}$, $R_{107}$, $R_{108}$, and $R_{109}$ are independently selected from hydrogen, $C_{1-6}$ alkyl, $C_{1-6}$ perfluoroalkyl, $C_{1-6}$ heteroalkyl, $C_{6-10}$ aryl, $C_{7-16}$ aralkyl, and $C_{5-10}$ heteroaryl.

In some embodiments, $R_{106}$, $R_{107}$, $R_{108}$, and $R_{109}$ are independently selected from hydrogen and alkyl.

In some embodiments, $R_{106}$, $R_{107}$, $R_{108}$, and $R_{109}$ are each hydrogen.

The compounds of the present disclosure can further include an anion $X^-$ selected from iodide, bromide, chloride, fluoride, triiodide, hydroxide, carbonate, bicarbonate, cyanide, acetate, nitrate, sulfate, phosphate, triflate, tosylate, tetrakis(3,5-bis(trifluoromethyl)phenyl)borate, bis(trifluoromethane)sulfonamide, and any combination thereof. The anion $X^-$ can counterbalances the positive charge in the compound.

In some embodiments, the compounds of Formula (I) is from the group consisting of:

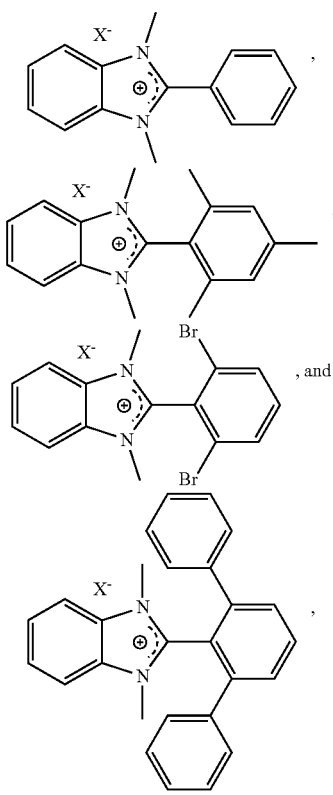

wherein $X^-$ is an anion selected from iodide, bromide, chloride, fluoride, triiodide, hydroxide, carbonate, bicarbonate, cyanide, acetate, nitrate, sulfate, phosphate, triflate, tosylate, tetrakis(3,5-bis(trifluoromethyl)phenyl)borate, bis(trifluoromethane)sulfonamide, and any combination thereof.

In some embodiments, a polymer includes a repeating unit derived from a compound above. The repeating unit derived from a benzimidazolium compound above can be incorporated into a polymer in any manner known to those of skill in the art. Particularly, the polymer can include a repeating unit derived from a compound of Formula (I) where groups $R_{103}$ and $R_{104}$ are linking moieties to other repeating units on a polymeric backbone.

In one embodiment, the benzimidazolium-containing compounds of the present disclosure are incorporated in a polymer backbone, as described in further experimental detail below. As used herein, a monomer that is part of the main chain (or backbone) of a polymer is a repeating unit that is connected on at least two ends to the polymer chain.

It will be appreciated that the moiety can be the only moiety in the backbone monomer: ─[─benzimidazolium-containing moiety─]$_x$. Alternatively, the moiety can be one of a plurality of moieties in the backbone of the monomer: [benzimidazolium-containing moiety]$_x$[A]$_y$[B]$_z$.

The present disclosure provides, inter alia, a polymer including at least one repeating units selected from Formula (II-A) and (II-B)

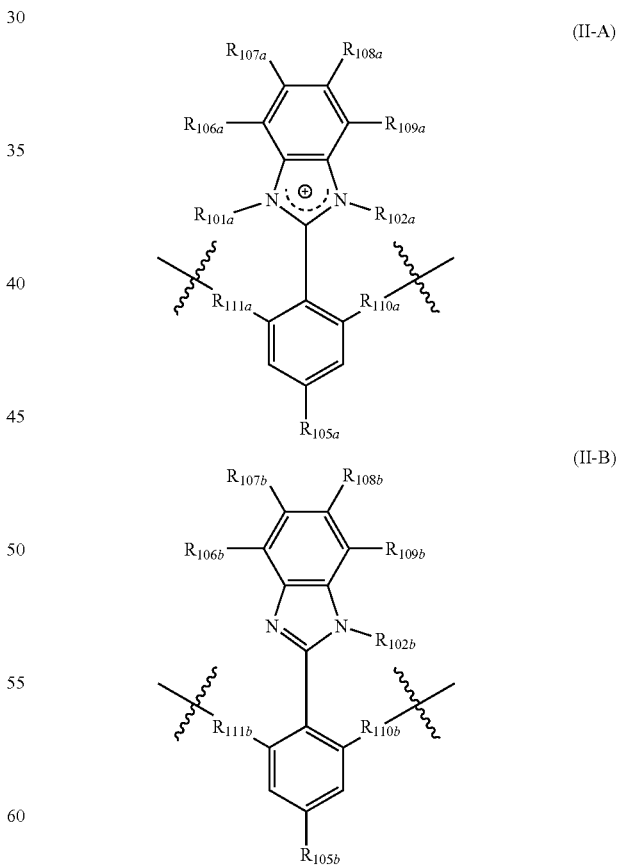

wherein:
$R_{101a}$, $R_{102a}$, and $R_{102b}$ are each independently selected from alkyl, perfluoroalkyl, heteroalkyl, aryl, aralkyl, and heteroaryl;

$R_{111a}$, $R_{110a}$, $R_{111b}$, and $R_{110b}$ are each independently selected from alkylene, perfluoroalkylene, heteroalkylene, arylene, aralkylene, heteroarylene, wherein said alkylene, perfluoroalkylene, heteroalkylene, arylene, aralkylene, or heteroarylene is each optionally substituted with 1, 2, 3, or 4 substituents independently selected from alkyl and halo;

$R_{105a}$ and $R_{105b}$ are each independently selected from hydrogen, alkyl, perfluoroalkyl, heteroalkyl, aryl, aralkyl, and heteroaryl;

$R_{106a}$, $R_{107a}$, $R_{108a}$, $R_{109a}$, $R_{106b}$, $R_{107b}$, $R_{108b}$, and $R_{109b}$ are each independently selected from hydrogen, alkyl, perfluoroalkyl, heteroalkyl, aryl, aralkyl, and heteroaryl.

The above-mentioned embodiments can be combined in any manner. For example, in some embodiments, the disclosure features a compound of Formula (I):

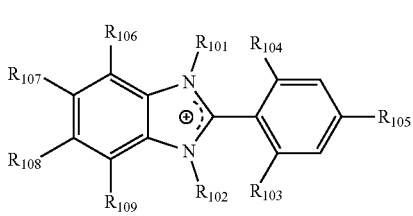

(I)

wherein $R_{101}$ and $R_{102}$ are each independently selected from $C_{1-10}$ alkyl, $C_{1-10}$ perfluoroalkyl, $C_{1-10}$ heteroalkyl, $C_{6-10}$ aryl, $C_{7-16}$ aralkyl, and $C_{5-10}$ heteroaryl;

$R_{103}$ and $R_{104}$ are each independently selected from hydrogen, $C_{1-10}$ alkyl, $C_{1-10}$ perfluoroalkyl, $C_{1-10}$ heteroalkyl, $C_{6-10}$ aryl, $C_{7-16}$ aralkyl, $C_{5-10}$ heteroaryl, and halo, wherein said $C_{1-10}$ alkyl, $C_{1-10}$ perfluoroalkyl, $C_{1-10}$ heteroalkyl, $C_{6-10}$ aryl, $C_{7-16}$ aralkyl, or $C_{5-10}$ heteroaryl is each optionally substituted with 1, 2, 3, or 4 substituents independently selected from alkyl and halo;

$R_{105}$ is selected from hydrogen, $C_{1-10}$ alkyl, $C_{1-10}$ perfluoroalkyl, $C_{1-10}$ heteroalkyl, $C_{6-10}$ aryl, $C_{7-16}$ aralkyl, and $C_{5-10}$ heteroaryl; and $R_{106}$, $R_{107}$, $R_{108}$, and $R_{109}$ are independently selected from hydrogen, $C_{1-10}$ alkyl, $C_{1-10}$ perfluoroalkyl, $C_{1-10}$ heteroalkyl, $C_{6-10}$ aryl, $C_{7-16}$ aralkyl, and $C_{5-10}$ heteroaryl.

In some embodiments, $R_{101}$ and $R_{102}$ are each independently selected from $C_{1-6}$ alkyl, $C_{1-6}$ perfluoroalkyl, $C_{1-6}$ heteroalkyl, $C_{6-10}$ aryl, $C_{7-16}$ aralkyl, and $C_{5-10}$ heteroaryl;

$R_{103}$ and $R_{104}$ are each independently selected from hydrogen, $C_{1-6}$ alkyl, $C_{1-6}$ perfluoroalkyl, $C_{1-6}$ heteroalkyl, $C_{6-10}$ aryl, $C_{7-16}$ aralkyl, $C_{5-10}$ heteroaryl, and halo, wherein said $C_{1-6}$ alkyl, $C_{1-6}$ perfluoroalkyl, $C_{1-6}$ heteroalkyl, $C_{6-10}$ aryl, $C_{7-16}$ aralkyl, or $C_{5-10}$ heteroaryl is each optionally substituted with 1, 2, 3, or 4 substituents independently selected from alkyl and halo;

$R_{105}$ is selected from hydrogen, $C_{1-6}$ alkyl, $C_{1-6}$ perfluoroalkyl, $C_{1-6}$ heteroalkyl, $C_{6-10}$ aryl, $C_{7-16}$ aralkyl, and $C_{5-10}$ heteroaryl; and $R_{106}$, $R_{107}$, $R_{108}$, and $R_{109}$ are independently selected from hydrogen, $C_{1-6}$ alkyl, $C_{1-6}$ perfluoroalkyl, $C_{1-6}$ heteroalkyl, $C_{6-10}$ aryl, $C_{7-16}$ aralkyl, and $C_{5-10}$ heteroaryl.

In some embodiments, $R_{101}$ and $R_{102}$ are each independently selected from alkyl and perfluoroalkyl;

$R_{103}$ and $R_{104}$ are each independently selected from alkyl, aryl, and halo, wherein said alkyl or aryl is each optionally substituted with 1, 2, 3, or 4 substituents independently selected from alkyl and halo;

$R_{105}$ is selected from hydrogen and alkyl; and $R_{106}$, $R_{107}$, $R_{108}$, and $R_{109}$ are independently selected from hydrogen and alkyl.

In some embodiments, $R_{101}$ and $R_{102}$ are each independently selected from alkyl and perfluoroalkyl;

$R_{103}$ and $R_{104}$ are each independently selected from alkyl, aryl, and halo;

$R_{105}$ is selected from hydrogen and alkyl; and $R_{106}$, $R_{107}$, $R_{108}$, and $R_{109}$ are independently selected from hydrogen and alkyl.

In some embodiments, $R_{101}$ and $R_{102}$ are each independently selected from alkyl;

$R_{103}$ and $R_{104}$ are each independently selected from alkyl, aryl, and halo;

$R_{105}$ is selected from hydrogen and alkyl; and $R_{106}$, $R_{107}$, $R_{108}$, and $R_{109}$ are each hydrogen.

The present disclosure also provides, inter alia, a polymer including repeating units selected of Formula (II-A) and (II-B)

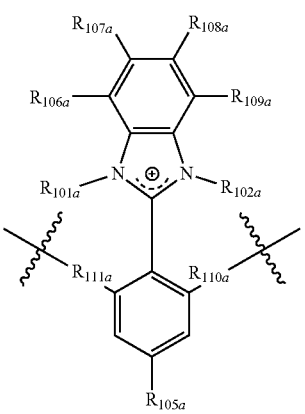

(II-A)

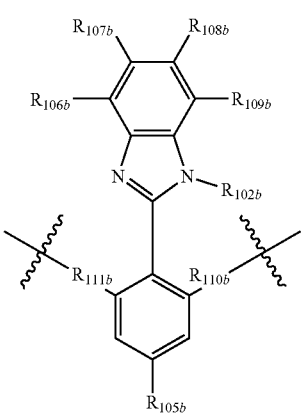

(II-B)

wherein:

$R_{101a}$, $R_{102a}$, and $R_{102b}$ are each independently selected from alkyl, perfluoroalkyl, heteroalkyl, aryl, aralkyl, and heteroaryl;

$R_{111a}$, $R_{110a}$, $R_{111b}$, and $R_{110b}$ are each independently selected from alkylene, perfluoroalkylene, heteroalkylene, arylene, aralkylene, heteroarylene, wherein said alkylene, perfluoroalkylene, heteroalkylene, arylene, aralkylene, or heteroarylene is each optionally substituted with 1, 2, 3, or 4 substituents independently selected from alkyl and halo;

$R_{105a}$ and $R_{105b}$ are each independently selected from hydrogen, alkyl, perfluoroalkyl, heteroalkyl, aryl, aralkyl, and heteroaryl;

$R_{106a}$, $R_{107a}$, $R_{108a}$, $R_{109a}$, $R_{106b}$, $R_{107b}$, $R_{108b}$, and $R_{109b}$ are each independently selected from hydrogen, alkyl, perfluoroalkyl, heteroalkyl, aryl, aralkyl, and heteroaryl, wherein the polymer comprises comprising r mole percentage repeating units of Formula (II-A), and s mole percentage repeating units of Formula (II-B), and r is from 1 mole percent to 100 mole percent, s is from 0 mole percent to 99 mole percent, and r+s=100%.

In some embodiments, the disclosure features a polymer including repeating units of Formula (II-A)

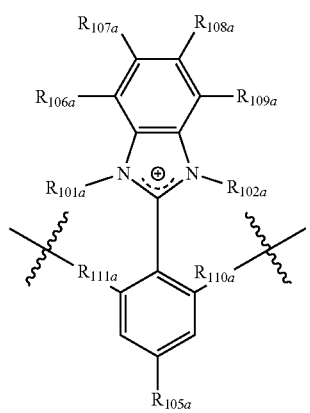

(II-A)

wherein:

$R_{101 1a}$ and $R_{102a}$ are each independently selected from alkyl, perfluoroalkyl, heteroalkyl, aryl, aralkyl, and heteroaryl;

$R_{111a}$ and $R_{110a}$ are each independently selected from alkylene, perfluoroalkylene, heteroalkylene, arylene, aralkylene, heteroarylene, wherein said alkylene, perfluoroalkylene, heteroalkylene, arylene, aralkylene, or heteroarylene is each optionally substituted with 1, 2, 3, or 4 substituents independently selected from alkyl and halo;

$R_{105a}$ is selected from hydrogen, alkyl, perfluoroalkyl, heteroalkyl, aryl, aralkyl, and heteroaryl;

$R_{106a}$, $R_{107a}$, $R_{108a}$, and $R_{109a}$ are each independently selected from hydrogen, alkyl, perfluoroalkyl, heteroalkyl, aryl, aralkyl, and heteroaryl.

In some embodiments, $R_{101a}$, $R_{102a}$, and $R_{102b}$ are each independently selected from $C_{1-10}$ alkyl, $C_{1-10}$ perfluoroalkyl, $C_{1-10}$ heteroalkyl, $C_{6-10}$ aryl, $C_{7-16}$ aralkyl, and $C_{5-10}$ heteroaryl.

In some embodiments, $R_{101a}$, $R_{102a}$, and $R_{102b}$ are each independently selected from $C_{1-6}$ alkyl, $C_{1-6}$ perfluoroalkyl, $C_{1-6}$ heteroalkyl, $C_{6-10}$ aryl, $C_{7-16}$ aralkyl, and $C_{5-10}$ heteroaryl.

In some embodiments, $R_{101a}$, $R_{102a}$, and $R_{102b}$ are each independently selected from alkyl, perfluoroalkyl, and heteroalkyl.

In some embodiments, $R_{101a}$, $R_{102a}$, and $R_{102b}$ are each independently selected from alkyl and perfluoroalkyl.

In some embodiments, $R_{101a}$, $R_{102a}$, and $R_{102b}$ are each independently alkyl.

In some embodiments, $R_{101a}$, $R_{102a}$, and $R_{102b}$ are each independently selected from methyl and ethyl.

In some embodiments, $R_{101a}$, $R_{102a}$, and $R_{102b}$ are each methyl.

In some embodiments, $R_{111a}$, $R_{110a}$, $R_{111b}$, and $R_{110b}$ are each independently selected from $C_{1-10}$ alkylene, $C_{1-10}$ perfluoroalkylene, $C_{1-10}$ heteroalkylene, $C_{6-10}$ arylene, $C_{7-16}$ aralkylene, $C_{5-10}$ heteroarylene, wherein said $C_{1-10}$ alkylene, $C_{1-10}$ perfluoroalkylene, $C_{1-10}$ heteroalkylene, $C_{6-10}$ arylene, $C_{7-16}$ aralkylene, or $C_{5-10}$ heteroarylene is each optionally substituted with 1, 2, 3, or 4 substituents independently selected from $C_{1-10}$ alkyl and halo.

In some embodiments, $R_{111a}$, $R_{110a}$, $R_{111b}$, and $R_{110b}$ are each independently selected from $C_{1-6}$ alkylene, $C_{1-6}$ perfluoroalkylene, $C_{1-6}$ heteroalkylene, $C_{6-10}$ arylene, $C_{7-16}$ aralkylene, $C_{5-10}$ heteroarylene, wherein said $C_{1-6}$ alkylene, $C_{1-6}$ perfluoroalkylene, $C_{1-6}$ heteroalkylene, $C_{6-10}$ arylene, $C_{7-16}$ aralkylene, or $C_{5-10}$ heteroarylene is each optionally substituted with 1, 2, 3, or 4 substituents independently selected from $C_{1-6}$ alkyl and halo.

In some embodiments, $R_{111a}$, $R_{110a}$, $R_{111b}$, and $R_{110b}$ are each independently selected from alkylene, perfluoroalkylene, heteroalkylene, arylene, and heteroarylene, wherein said alkylene, perfluoroalkylene, heteroalkylene, arylene, and heteroarylene is each optionally substituted with 1, 2, 3, or 4 substituents independently selected from alkyl and halo.

In some embodiments, $R_{111a}$, $R_{110a}$, $R_{111b}$, and $R_{110b}$ are each independently selected from alkylene, perfluoroalkylene, and arylene, wherein said alkylene, perfluoroalkylene, or arylene is each optionally substituted with 1, 2, 3, or 4 substituents independently selected from alkyl and halo.

In some embodiments, $R_{111a}$, $R_{110a}$, $R_{111b}$, and $R_{110b}$ are each independently selected from alkylene and arylene, wherein said alkylene or arylene is each optionally substituted with 1, 2, 3, or 4 substituents independently selected from alkyl and halo.

In some embodiments, $R_{111a}$, $R_{110a}$, $R_{111b}$, and $R_{110b}$ are each independently arylene, wherein said arylene is optionally substituted with 1, 2, 3, or 4 substituents independently selected from alkyl and halo.

In some embodiments, $R_{111a}$, $R_{110a}$, $R_{111b}$, and $R_{110b}$ are each phenylene, wherein said phenylene is optionally substituted with 1, 2, 3, or 4 substituents independently selected from alkyl and halo.

In some embodiments, $R_{105a}$ and $R_{105b}$ are each independently selected from hydrogen, $C_{1-10}$ alkyl, $C_{1-10}$ perfluoroalkyl, $C_{1-10}$ heteroalkyl, $C_{6-10}$ aryl, $C_{7-16}$ aralkyl, and $C_{5-10}$ heteroaryl.

In some embodiments, $R_{105a}$ and $R_{105b}$ are each independently selected from hydrogen, $C_{1-6}$ alkyl, $C_{1-6}$ perfluoroalkyl, $C_{1-6}$ heteroalkyl, $C_{6-10}$ aryl, $C_{7-16}$ aralkyl, and $C_{5-10}$ heteroaryl.

In some embodiments, $R_{105a}$ and $R_{105b}$ are each independently selected from hydrogen, alkyl, perfluoroalkyl, heteroalkyl, aryl, and heteroaryl.

In some embodiments, $R_{105a}$ and $R_{105b}$ are each independently selected from hydrogen, alkyl, aryl, and heteroaryl.

In some embodiments, $R_{105a}$ and $R_{105b}$ are each independently selected from hydrogen and alkyl.

In some embodiments, $R_{105a}$ and $R_{105b}$ are each independently selected from hydrogen and methyl.

In some embodiments, $R_{106a}$, $R_{107a}$, $R_{108a}$, $R_{109a}$, $R_{106b}$, $R_{107b}$, $R_{108b}$, and $R_{109b}$ are each independently selected from hydrogen, $C_{1-10}$ alkyl, $C_{1-10}$ perfluoroalkyl, $C_{1-10}$ heteroalkyl, $C_{6-10}$ aryl, $C_{7-16}$ aralkyl, and $C_{5-10}$ heteroaryl.

In some embodiments, $R_{106a}$, $R_{107a}$, $R_{108a}$, $R_{109a}$, $R_{106b}$, $R_{107b}$, $R_{108b}$, and $R_{109b}$ are each independently selected from hydrogen, $C_{1-6}$ alkyl, $C_{1-6}$ perfluoroalkyl, $C_{1-6}$ heteroalkyl, $C_{6-10}$ aryl, $C_{7-16}$ aralkyl, and $C_{5-10}$ heteroaryl.

In some embodiments, $R_{106a}$, $R_{107a}$, $R_{108a}$, and $R_{109a}$, $R_{106b}$, $R_{107b}$, $R_{108b}$, and $R_{109b}$ are independently selected from hydrogen and alkyl.

In some embodiments, $R_{106a}$, $R_{107a}$, $R_{108a}$, and $R_{109a}$, $R_{106b}$, $R_{107b}$, $R_{108b}$, and $R_{109b}$ are each hydrogen.

In some embodiments, the polymer includes r mole percentage repeating units of Formula (II-A), and s mole percentage repeating units of Formula (II-B), and r is from 1 mole percent to 95 mole percent,
s is from 5 mole percent to 99 mole percent, and
r+s=100%.

In some embodiments, s is 0 mole percent.

The above-mentioned embodiments can be combined in any manner. For example, in some embodiments, the present disclosure features a polymer including repeating units selected of Formula (II-A) and (II-B)

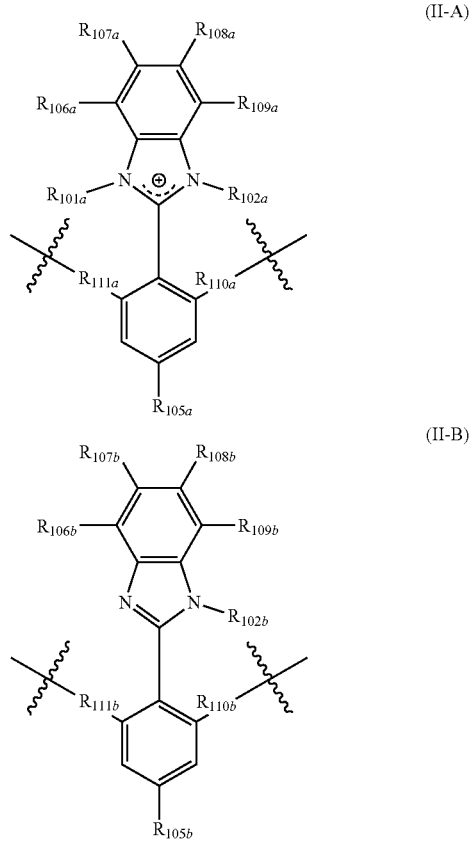

wherein:
$R_{101a}$, $R_{102a}$, and $R_{102b}$ are each independently selected from $C_{1-10}$ alkyl, $C_{1-10}$ perfluoroalkyl, $C_{1-10}$ heteroalkyl, $C_{6-10}$ aryl, $C_{7-16}$ aralkyl, and $C_{5-10}$ heteroaryl;

$R_{111a}$, $R_{110a}$, $R_{111b}$, and $R_{110b}$ are each independently selected from $C_{1-10}$ alkylene, $C_{1-10}$ perfluoroalkylene, $C_{1-10}$ heteroalkylene, $C_{6-10}$ arylene, $C_{7-16}$ aralkylene, $C_{5-10}$ heteroarylene, wherein said $C_{1-10}$ alkylene, $C_{1-10}$ perfluoroalkylene, $C_{1-10}$ heteroalkylene, $C_{6-10}$ arylene, $C_{7-16}$ aralkylene, or $C_{5-10}$ heteroarylene is each optionally substituted with 1, 2, 3, or 4 substituents independently selected from $C_{1-10}$ alkyl and halo;

$R_{105a}$ and $R_{105b}$ are each independently selected from hydrogen, $C_{1-10}$ alkyl, $C_{1-10}$ perfluoroalkyl, $C_{1-10}$ heteroalkyl, $C_{6-10}$ aryl, $C_{7-16}$ aralkyl, and $C_{5-10}$ heteroaryl;

$R_{106a}$, $R_{107a}$, $R_{108a}$, $R_{109a}$, $R_{106b}$, $R_{107b}$, $R_{108b}$, and $R_{109b}$ are each independently selected from hydrogen, $C_{1-10}$ alkyl, $C_{1-10}$ perfluoroalkyl, $C_{1-10}$ heteroalkyl, $C_{6-10}$ aryl, $C_{7-16}$ aralkyl, and $C_{5-10}$ heteroaryl; and the polymer includes r mole percentage repeating units of Formula (II-A), and s mole percentage repeating units of Formula (II-B), and r is from 1 mole percent to 100 mole percent,
s is from 0 mole percent to 99 mole percent, and
r+s=100%.

In some embodiments, $R_{101a}$, $R_{102a}$, and $R_{102b}$ are each independently selected from $C_{1-6}$ alkyl, $C_{1-6}$ perfluoroalkyl, $C_{1-6}$ heteroalkyl, $C_{6-10}$ aryl, $C_{7-16}$ aralkyl, and $C_{5-10}$ heteroaryl;

$R_{111a}$, $R_{110a}$, $R_{111b}$, and $R_{110b}$ are each independently selected from $C_{1-6}$ alkylene, $C_{1-6}$ perfluoroalkylene, $C_{1-6}$ heteroalkylene, $C_{6-10}$ arylene, $C_{7-16}$ aralkylene, $C_{5-10}$ heteroarylene, wherein said $C_{1-6}$ alkylene, $C_{1-6}$ perfluoroalkylene, $C_{1-6}$ heteroalkylene, $C_{6-10}$ arylene, $C_{7-16}$ aralkylene, or $C_{5-10}$ heteroarylene is each optionally substituted with 1, 2, 3, or 4 substituents independently selected from $C_{1-6}$ alkyl and halo;

$R_{105a}$ and $R_{105b}$ are each independently selected from hydrogen, $C_{1-6}$ alkyl, $C_{1-6}$ perfluoroalkyl, $C_{1-6}$ heteroalkyl, $C_{6-10}$ aryl, $C_{7-16}$ aralkyl, and $C_{5-10}$ heteroaryl;

$R_{106a}$, $R_{107a}$, $R_{108a}$, $R_{109a}$, $R_{106b}$, $R_{107b}$, $R_{108b}$, and $R_{109b}$ are each independently selected from hydrogen, $C_{1-6}$ alkyl, $C_{1-6}$ perfluoroalkyl, $C_{1-6}$ heteroalkyl, $C_{6-10}$ aryl, $C_{7-16}$ aralkyl, and $C_{5-10}$ heteroaryl; and the polymer includes r mole percentage repeating units of Formula (II-A), and s mole percentage repeating units of Formula (II-B), and r is from 1 mole percent to 100 mole percent,
s is from 0 mole percent to 99 mole percent, and
r+s=100%.

In some embodiments, $R_{101a}$, $R_{102a}$, and $R_{102b}$ are each independently alkyl; $R_{111a}$, $R_{110a}$, $R_{111b}$, and $R_{110b}$ are each independently selected from alkylene and arylene, wherein said alkylene or arylene is each optionally substituted with 1, 2, 3, or 4 substituents independently selected from alkyl and halo;

$R_{105a}$ and $R_{105b}$ are each independently selected from hydrogen and alkyl;

$R_{106a}$, $R_{107a}$, $R_{108a}$, and $R_{109a}$, $R_{106b}$, $R_{107b}$, $R_{108b}$, and $R_{109b}$ are independently selected from hydrogen and alkyl; and the polymer includes r mole percentage repeating units of Formula (II-A), and s mole percentage repeating units of Formula (II-B), and r is from 1 mole percent to 100 mole percent,
s is from 0 mole percent to 99 mole percent, and
r+s=100%.

In some embodiments, $R_{101a}$, $R_{102a}$, and $R_{102b}$ are each independently alkyl;

$R_{111a}$, $R_{110a}$, $R_{111b}$, and $R_{110b}$ are each independently arylene, wherein said arylene is optionally substituted with 1, 2, 3, or 4 substituents independently selected from alkyl and halo;

$R_{105a}$ and $R_{105b}$ are each independently selected from hydrogen and alkyl;

$R_{106a}$, $R_{107a}$, $R_{108a}$, and $R_{109a}$, $R_{106b}$, $R_{107b}$, $R_{108b}$, and $R_{109b}$ are each hydrogen; and the polymer includes r mole percentage repeating units of Formula (II-A), and s mole percentage repeating units of Formula (II-B), and r is from 1 mole percent to 100 mole percent,
s is from 0 mole percent to 99 mole percent, and
r+s=100%.

The polymer can further include one or more anions $X^-$ selected from iodide, bromide, chloride, fluoride, triiodide, hydroxide, carbonate, bicarbonate, cyanide, acetate, nitrate, sulfate, phosphate, triflate, tosylate, tetrakis(3,5-bis(trifluoromethyl)phenyl)borate, bis(trifluoromethane)sulfonamide, and any combination thereof, wherein the one or more anions $X^-$ counterbalance the positive charges in the polymer.

The polymer can be a copolymer, such as a random copolymer, or a block copolymer. Block copolymers can be made, for example, as described in Maity S. and Jana T., *Appl. Mater. Interfaces*, 2014, 6 (9), pp 6851-6864. For example, two separate homopolymers can be synthesized and then reacted together in another polymerization to provide a block copolymer. Post-polymerization functionalization can then provide block copolymers having ionic amine backbones, where N-substitution is randomly distributed along the polymer chain.

General Synthetic Scheme

The polymers of the present disclosure can be prepared in a variety of ways known to one skilled in the art of organic synthesis. The polymers of the present disclosure can be synthesized using the methods as hereinafter described below and in the Examples, together with synthetic methods known in the art of synthetic organic chemistry or variations thereon as appreciated by those skilled in the art.

The polymers of this disclosure can be prepared from readily available starting materials using the following general methods and procedures. It will be appreciated that where typical or preferred process conditions (i.e., reaction temperatures, times, mole ratios of reactants, solvents, pressures, etc.) are given; other process conditions can also be used unless otherwise stated. Optimum reaction conditions may vary with the particular reactants or solvent used, but such conditions can be determined by one skilled in the art by routine optimization procedures.

The processes described herein can be monitored according to any suitable method known in the art. For example, product formation can be monitored by spectroscopic means, such as nuclear magnetic resonance spectroscopy (e.g., $^1H$ or $^{13}C$) infrared spectroscopy, spectrophotometry (e.g., UV-visible), or mass spectrometry, or by chromatography such as high performance liquid chromatography (HPLC) or thin layer chromatography.

Preparation of polymers and compounds can involve the protection and deprotection of various chemical groups. The need for protection and deprotection, and the selection of appropriate protecting groups can be readily determined by one skilled in the art. The chemistry of protecting groups can be found, for example, in Greene, et al., *Protective Groups in Organic Synthesis*, 4th. Ed., Wiley & Sons, 2006.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected.

The polymers and compounds of the disclosure can be prepared, for example, using the reaction pathways and techniques as described in Scheme 1, in the Examples below. In some embodiments, once a neutral polymer having a benzimidazole moiety has been synthesized, the polymer can be functionalized to provide a cationic N-substituted polymer.

The N-substitution can include dissolving a neutral polymer in a suitable organic solvent (e.g., N-methyl-2-pyrrolidone, NMP) to provide a polymer solution; adding a known amount of an alkyl halide to the polymer solution and stirring the polymer solution for a period of time to provide the cationic N-substituted polymer.

Membrane Formation

In another aspect, an ionic membrane is provided. In one embodiment, the ionic membrane includes a polymer including at least one repeating unit selected from Formula (II-A) and (II-B) (e.g., Formula (II-A)), as described above. As an example, the ionic membrane can include a polymer including repeating units of Formula (II-A) and (II-B) as described above. The membranes created from these polymers are stable in high pH environments, a feat that most present technologies are not capable of withstanding.

In some embodiments, the polymers of the present disclosure can be readily dissolved in alcoholic solvents, such as methanol, ethanol, and propanol, as well as organic solvents, such as dimethylsulfoxide. Once dissolved, the polymeric solution can be drop-cast onto a substrate, and a free-standing film of the polymer can be obtained once the solvent has evaporated under appropriately controlled temperature and pressure conditions. In other embodiments, a solution including a dissolved polymer can be spray-coated, dip-coated, or otherwise applied onto a substrate.

In the Example below, benzimidazolium hydroxide compounds, in which the C2-position is attached to a phenyl group possessing hydrogen, bromide, methyl, or phenyl at the ortho positions, were prepared and investigated for stability in a quantitative alkaline stability test.

Example

Benzimidazolium hydroxide compounds, in which the C2-position (i.e., the carbon between the two nitrogen atoms in the benzimidazolium moiety) is attached to a phenyl group possessing hydrogen, bromide, methyl, or phenyl at the ortho positions, were prepared and investigated for stability in a quantitative alkaline stability test. The differences between the stability of the various protecting groups in caustic solutions are rationalized on the basis of their crystal structures and DFT calculations. The highest stability was observed for the m-terphenyl-protected benzimidazolium, showing a half-life in 3 M $NaOD/CD_3OD/D_2O$ at 80° C. of 3240 h. A high molecular weight polymer analogue of this model compound was prepared that exhibited excellent mechanical properties, high ionic conductivity and ion-exchange capacity, as well as remarkable hydroxide stability in alkaline solutions: only 5% degradation after 168 h in 2 M KOH at 80° C. This represented the most stable aqueous, hydroxide-conducting benzimidazolium polymer to date.

Differences in hydroxide-stability of four o-substituted phenylene C2-groups, each bearing either ortho-positioned hydrogen atoms (HB), bromide (BrB), methyl (MeB), or phenyl (PhB) were presented.

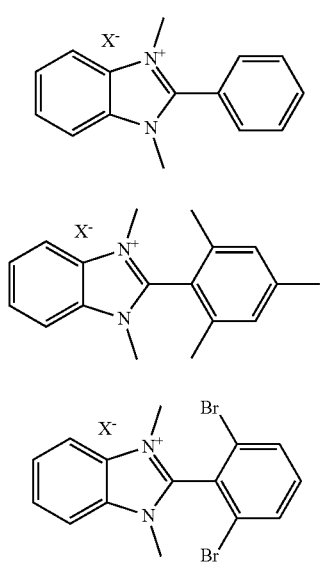

HB

5

MeB 10

BrB

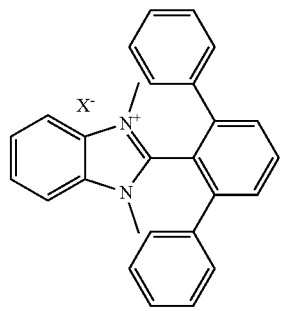

PhB

15

20

As BrB and PhB had never been reported, a novel and versatile synthetic route (Scheme 1) was designed to prepare functionalized aryl-protected benzimidazoliums on multi-gram scales. After directed ortho-metalation and electrophilic aromatic substitution of 1,3-dibromobenzene, an acid condensation yielded compound 2 in near quantitative yield. The controlled methylation of 2 to produce 3 allows access, via Suzuki coupling, to various aryl-protected benzimidazoles, such as 4 and 5. A second methylation of 3 and 4 yielded BrB and PhB, respectively. MeB and HB were prepared using Schemes S1 and S2.

Scheme 1. Synthetic route to the model compounds (BrB and PhB) and polymers PPB and PPMB.

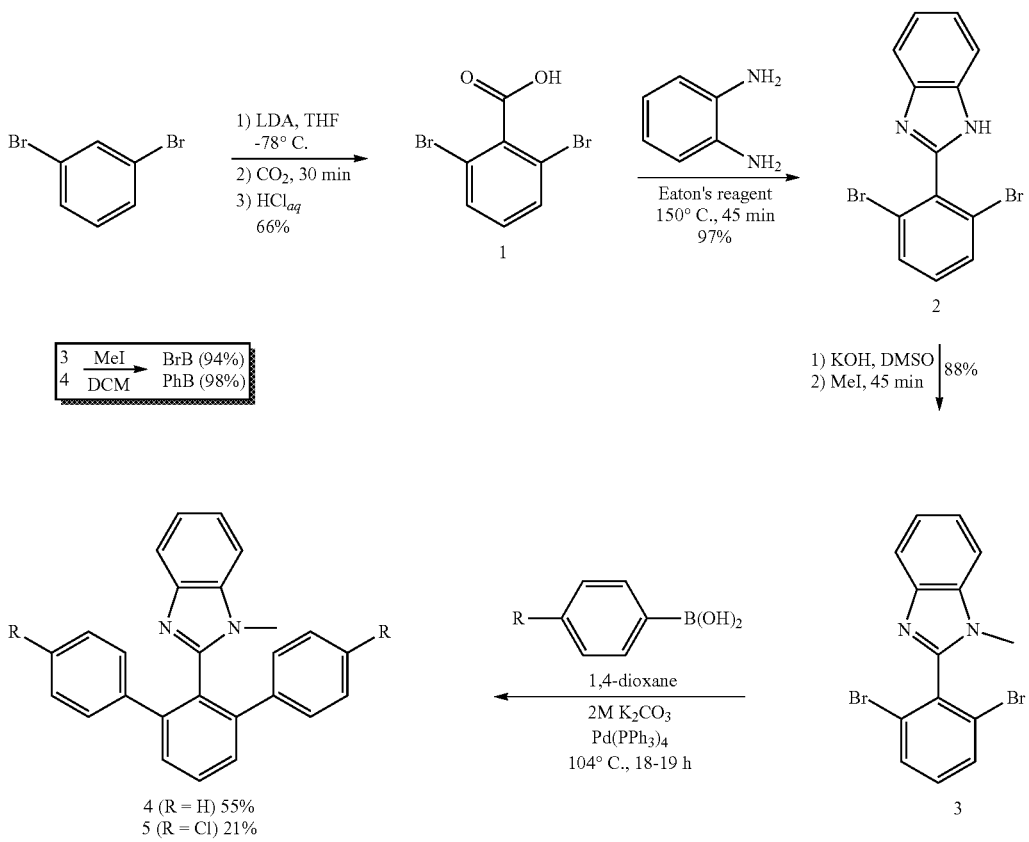

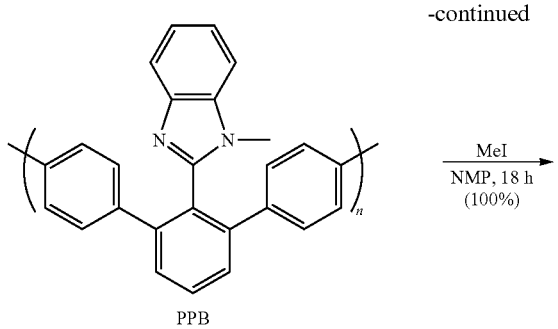

PPB

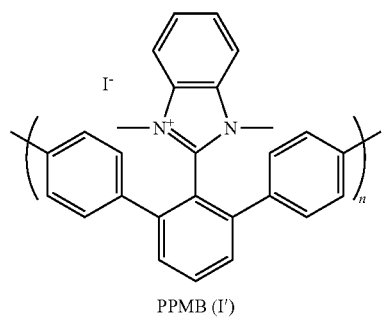

PPMB (I')

Each of the four model compounds was subjected to the same accelerated hydroxide stability test, which involved dissolution of the model compound (0.02 M) in 3 M NaOD/CD$_3$OD/D$_2$O (7:3 CD$_3$OD:D$_2$O by mass). The solutions were heated to 80° C. for up to 240 h. Aliquots were intermittently extracted and analyzed by $^1$H NMR spectroscopy (FIGS. 4-7). The extent of degradation was quantified using Equation S5 and plotted in FIG. 8.

Compound HB began degrading immediately after its dissolution in the basic solution at room temperature and was fully degraded to its amide product by time of the first measurement (FIG. 7), demonstrating extreme lability of un-protected benzimidazoliums in strongly alkaline media.

Figure 6:
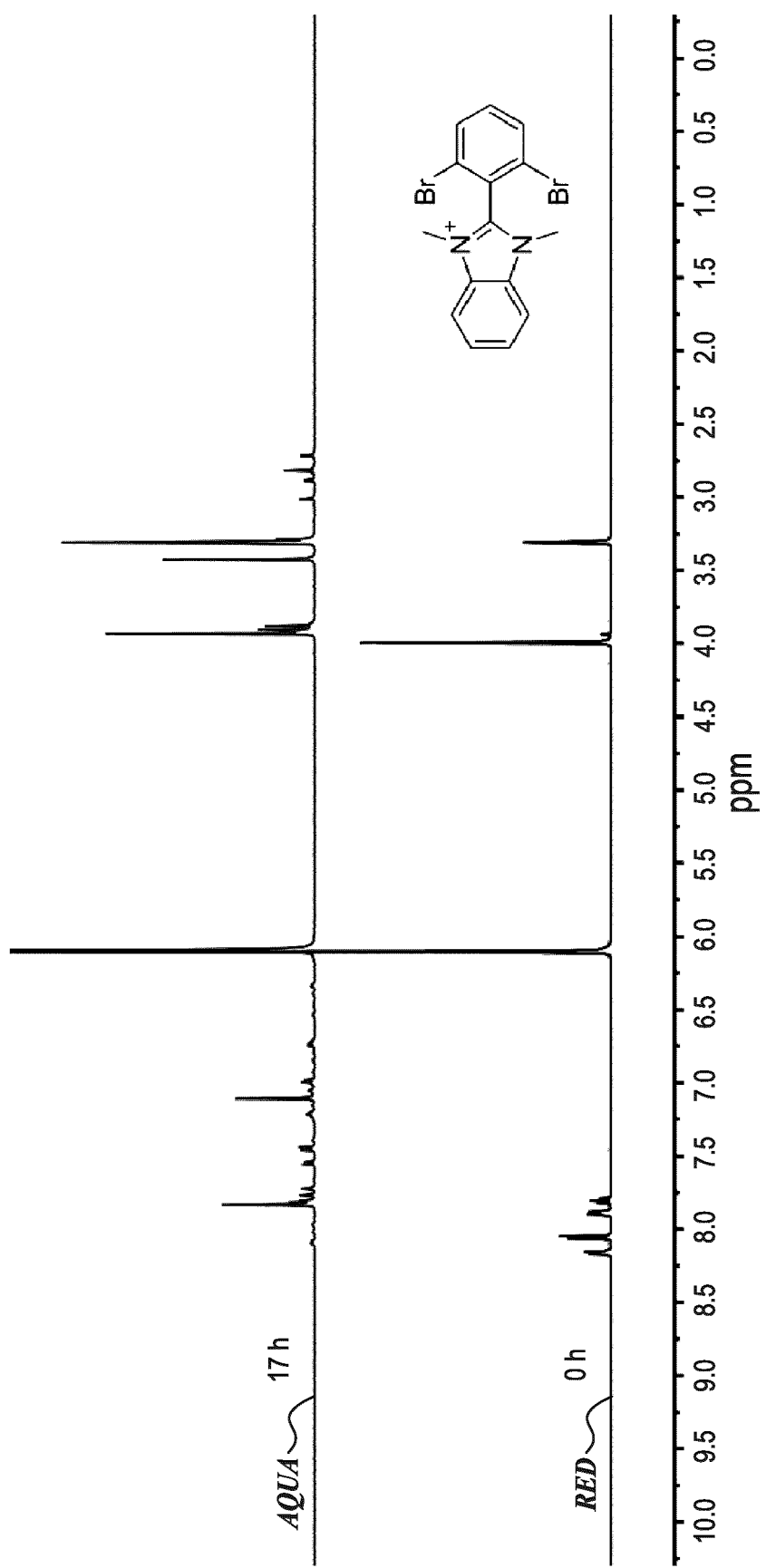
FIG. 6 shows $^1H$ NMR spectra of BrB (0.02 M) in 3 M $NaOD/CD_3OD/D_2O$ after heating at 80° C. for the specified duration.
Figure 7:
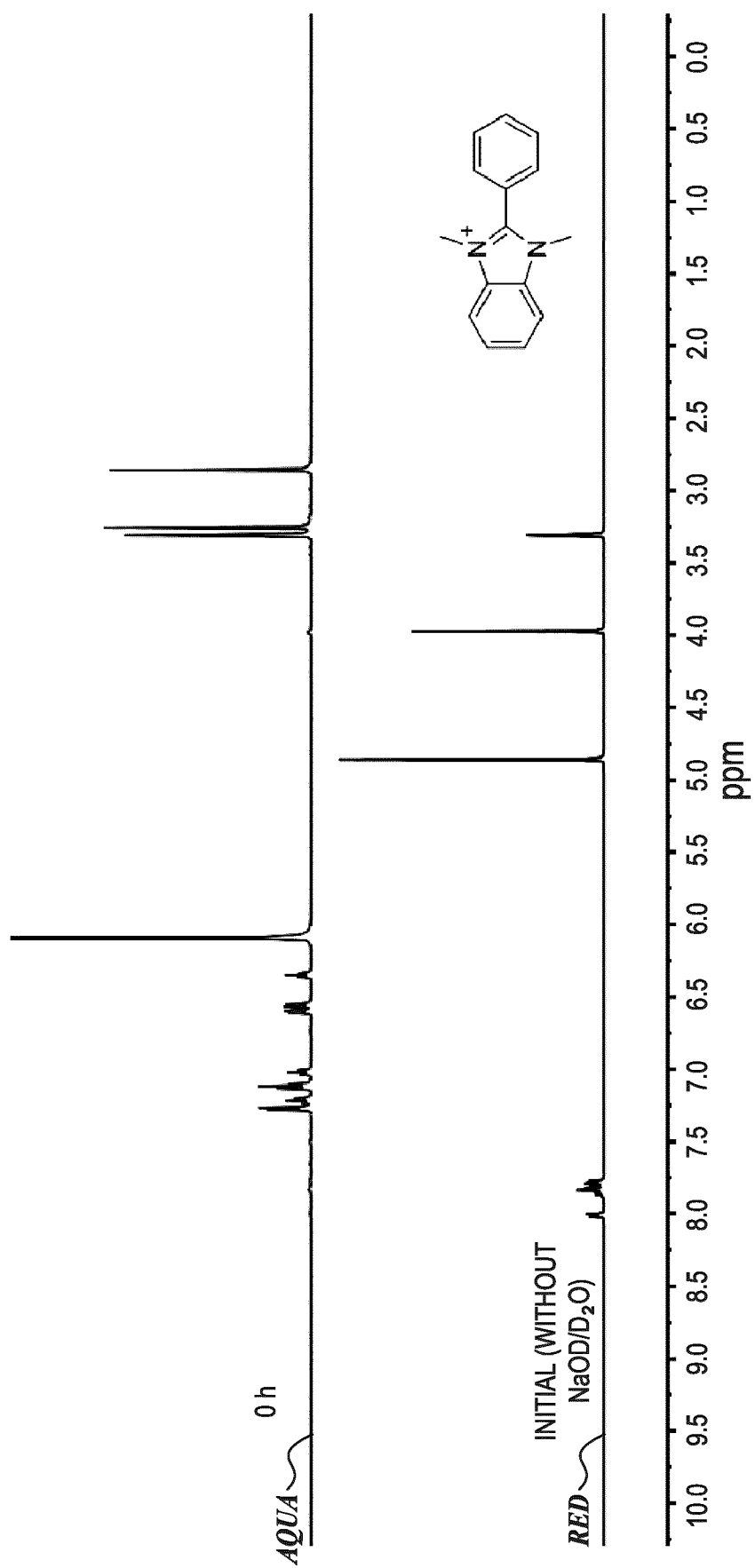
FIG. 7 shows $^1H$ NMR spectra of HB (0.02 M) in 3 M $NaOD/CD_3OD/D_2O$ taken after dissolution ("0 h") as well as HB (0.02 M) in pure $CD_3OD$ (without $NaOD/D_2O$).

BrB appeared stable at room temperature, but fully degraded after 16 h when the temperature was raised 80° C. (FIG. 6). The transition of the resonance from 4.00 ppm to 3.90 ppm in the $^1$H NMR spectrum suggested that new dimethylated benzimidazoliums were produced, which form from the nucleophilic displacement of bromide for hydroxyl groups, as well as amide products, which appear at 3.0-2.7 ppm.

Degradation of MeB and PhB followed exponential decay, indicative of a pseudo-first order reaction. By fitting the data to exponential functions, the rate constants and half-life ($t_{1/2}$) at 80° C. in those solutions were calculated, as shown in Table 1. The rate of degradation of PhB ($t_{1/2}$ 3240 h) was ~7 times slower than that of MeB ($t_{1/2}$ 436 h), which represented the highest alkaline stability for a benzimidazolium hydroxide reported to date.

Figure 9:
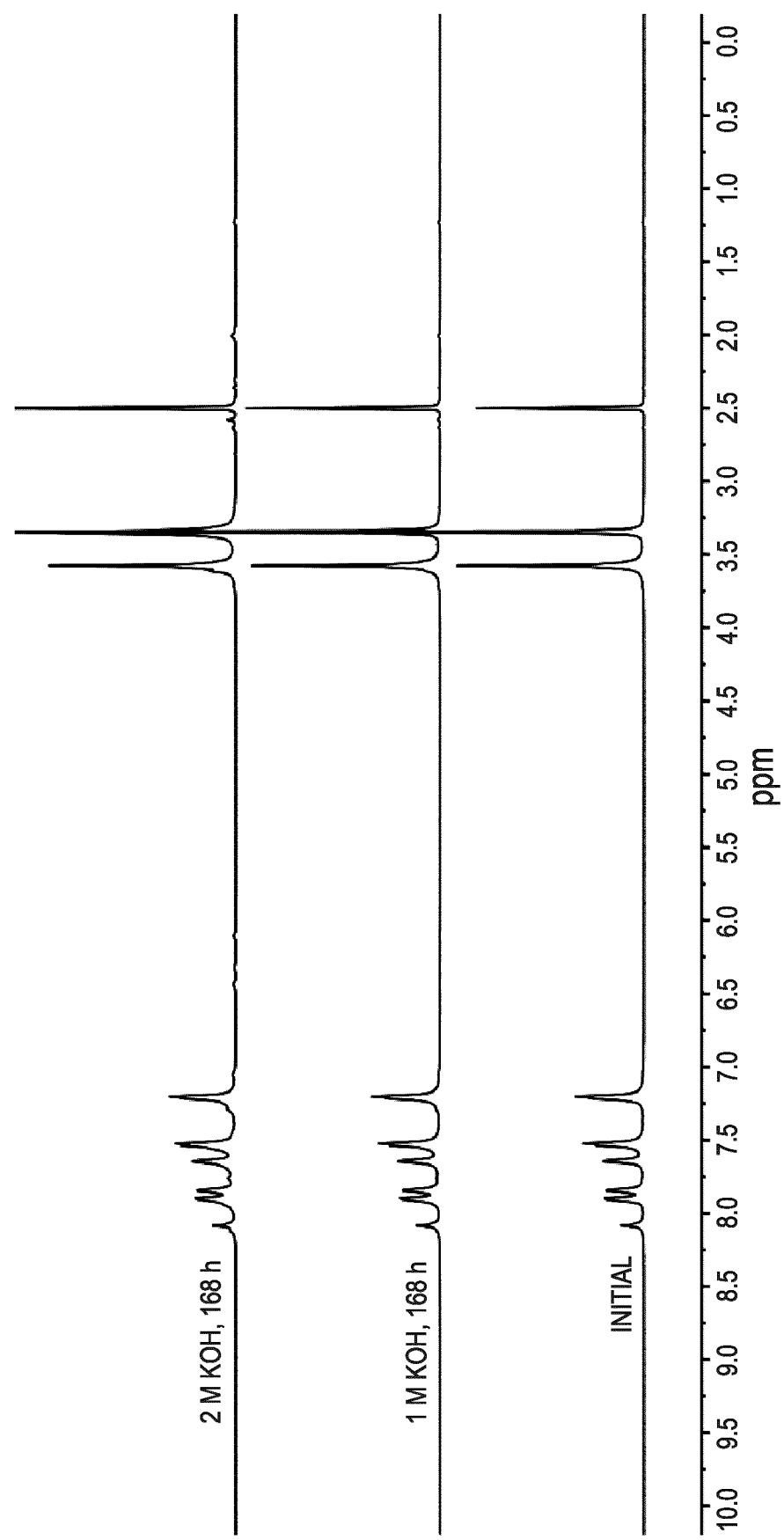
FIG. 9 shows $^1H$ NMR spectra of PPMB (chloride form) in DMSO-$d_6$ before ("initial") and after being subjected to either 1 M or 2 M $KOH_{aq.}$ at 80° C. for 168 h.
Figure 10:
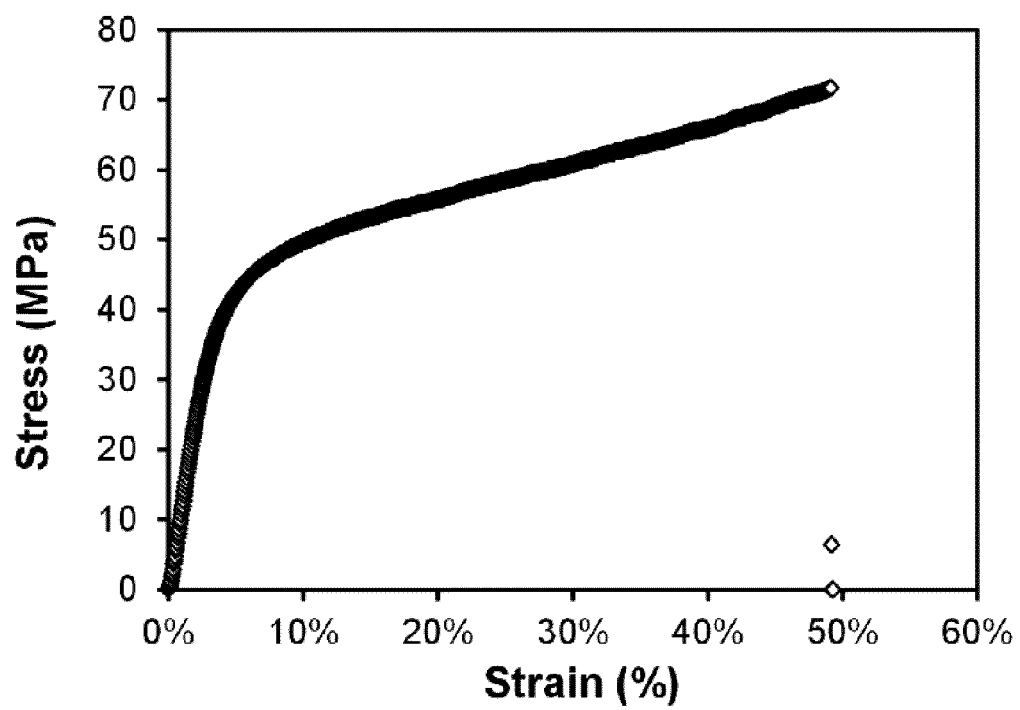
FIG. 10 is a graph showing a stress-strain curve of PPMB (iodide form) under ambient conditions (21° C., 42% RH) with a cross-head speed of 5.00 mm $min^{-1}$.

A polymeric analogue of PhB, PPMB (Scheme 1), was prepared. The neutral polymer, PPB, was prepared by Yamamoto coupling of 5 to produce a high molecular weight (intrinsic viscosity of 2.10 dL g$^{-1}$, FIG. 3) poly(phenylene) backbone bearing 1-methylbenzimidazole pendant groups. Complete methylation of PPB with iodomethane (MeI) produced PPMB in its iodide form. As a membrane, PPMB was strong and flexible, possessing a high tensile strength of 72 MPa, elongation at break of 49%, and Young's modulus of 1.29 GPa (FIG. 10). In its hydroxide form, the colourless and transparent film possessed an ion exchange capacity (IEC$_{OH^-}$) of 2.56 meq g$^{-1}$. In its fully hydrated state and in air, it exhibited a mixed hydroxide/carbonate ionic conductivity of 13.2±1.4 mS cm$^{-1}$ (22° C.), which is twice the conductivity of methyl-protected poly(benzimidazolium) of similar IEC and similar water uptake of 81±10%. After immersion of the membrane in 1 M or 2 M KOH at 80° C. for 168 h, only 1.7% and 5.3% degradation was observed, respectively (FIG. 9), which is unprecedented for a benzimidazolium-containing polymer.

Figure 11:
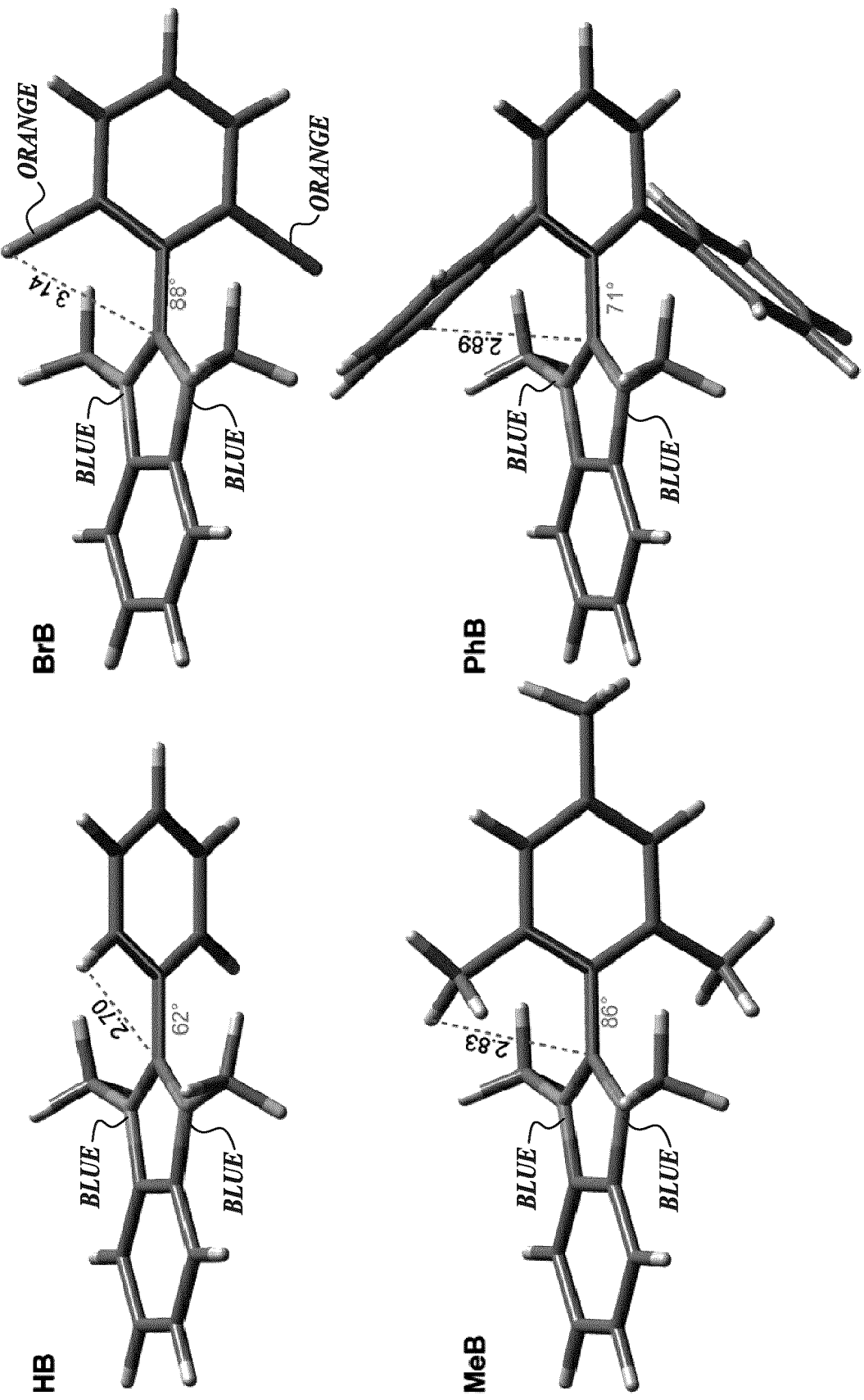
FIG. 11 shows the reagent DFT-calculated structures where the indicated dihedral angles were measured over the four atoms shown by the gray line (benzimidazolium plane compared to the 2-phenyl plane) and the dashed lines shown represent the shortest distance from the protecting group to the C2-carbon.
Figure 12:
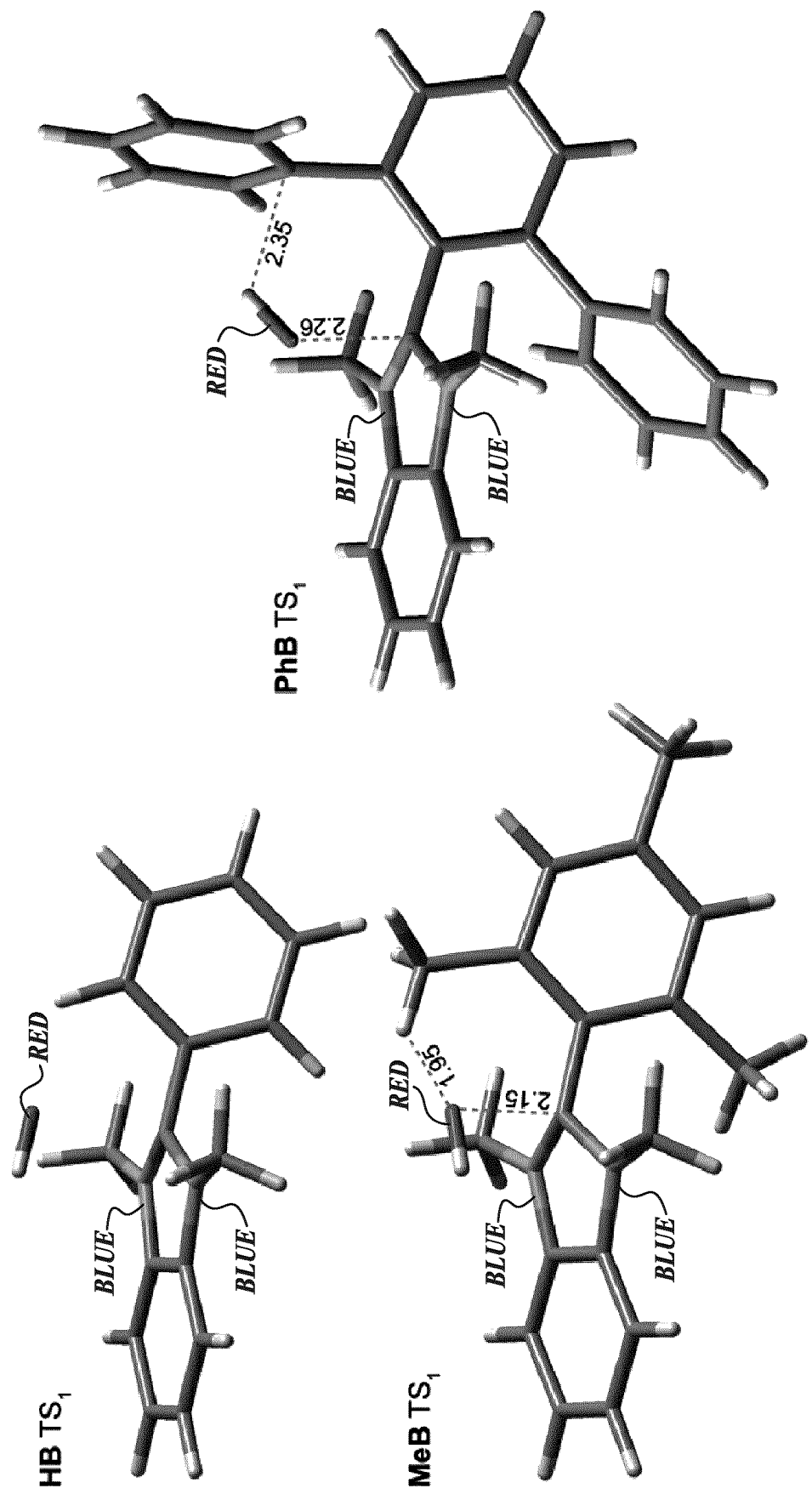
FIG. 12 shows the DFT structure of $TS_1$ for HB, MeB, and PhB.

In order to investigate the origin of the stability differences between the C2-protected benzimidazolium small molecules, single crystals were grown and characterized by XRD. In addition, the relative energies of their degradation pathways were explored using DFT calculations. Each compound was crystallized in its iodide form. Refined crystal structures are shown in FIG. 1. Using the crystal structures, the dihedral angles between the benzimidazolium plane and that of the C2-substituted phenyl plane (FIG. 11), as well as the shortest distance between the C2-carbon and iodide were measured (reported in Table 1).

TABLE 1

Properties of the model compounds based on experimental data and DFT calculations.

| Compound | Solid-state Dihedral angle[a] | Solution-state Dihedral angle[b] | C2-to-I$^-$ distance (Å)[c] | $t_{1/2}$ (h)[d] |
|---|---|---|---|---|
| HB | 54.40/55.02 | 62 | 3.704 | <0.1 |
| BrB[e] | 70.45/73.26 | 88 | 5.497 | <10 |
| | 73.08/81.92 | | 5.587 | |
| MeB | 79.21/83.77 | 86 | 4.743 | 436 |
| PhB | 65.03/68.58 | 71 | 6.218 | 3240 |

[a]Measured between the benzimidazolium and C2-phenyl planes in the iodide-form from XRD below 90°.
[b]DFT calculated solution structures.
[c]The shortest C2-carbon-to-iodide distance(s) for the iodide-form x-ray structures.
[d]The half-life of the compound dissolved in 3M NaOD/CD$_3$OD/D$_2$O at 80° C.
[e]BrB (XRD) possessed two unique structures within one unit cell.

The solid-state dihedral angles within each molecule were unique for each quadrant due to the non-planarity of the benzimidazolium ring. BrB possessed the largest variation of dihedral angles, and also possessed two molecular structures in its unit cell, leading to 8 different dihedral angles. The average dihedral angles increased in the order HB<PhB<BrB<MeB. As this trend did not follow the trend in half-life in strong base, the dihedral angle alone could not be used as a measure of hydroxide stability. However, the C2-carbon-to-iodide distance did match the trend in half-life, with the longer distance translating to a longer half-life. The exception to this trend is BrB, as its protecting bromide groups were strongly susceptible to nucleophilic displacement.

Figure 2:
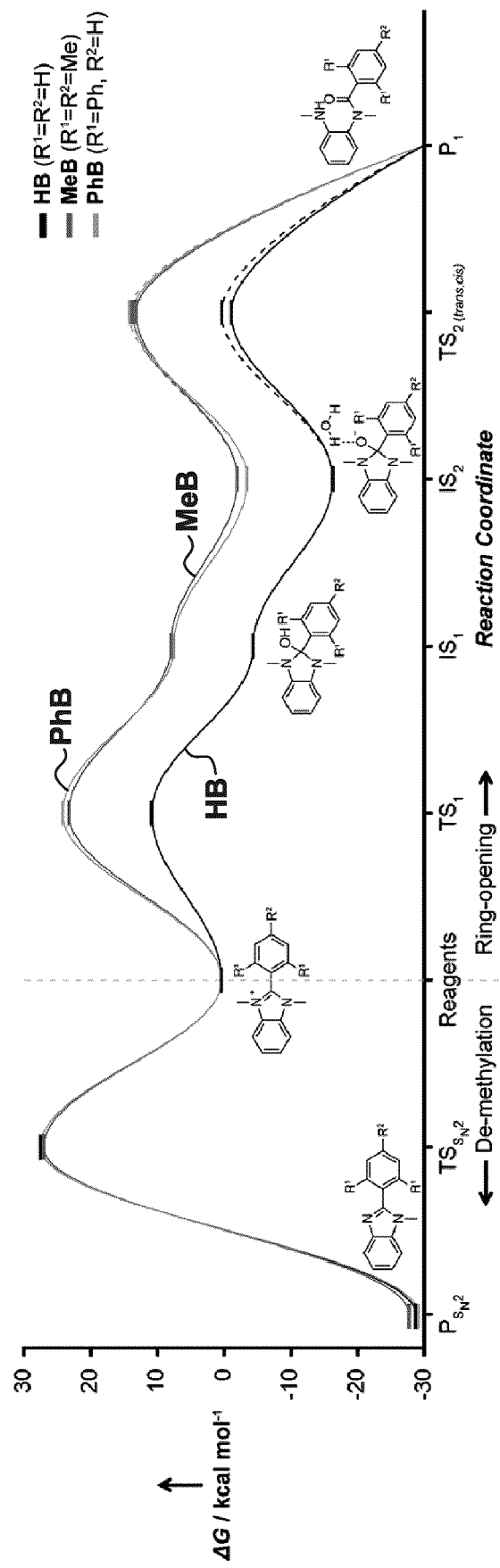
FIG. 2 is a graphical representation of reaction profiles for two hydroxide-mediated degradation pathways (de-methylation and ring-opening) for HB, MeB, and PhB. The dotted lines represent the higher energy, $TS_{2,trans}$, ring-opening degradation pathway. No barrier was found between $IS_1$ and $IS_2$

To compare the hydroxide stability differences between HB, MeB, and PhB, DFT was used to calculate the energy barriers and states along two possible degradation pathways, which were graphically displayed in FIG. 2. The overall reaction for each pathway is shown in Scheme 2. The first pathway represents the nucleophilic addition-elimination reaction of hydroxide on the C2-carbon of the benzimidazolium, resulting in the amide "ring-opened" product. The second pathway represents the nucleophilic substitution of hydroxide with the N-methyl carbon, resulting in a 2-substituted-1-methylbenzimidazole, which is referred to herein as "de-methylation" degradation.

As observed in FIG. 2, the nucleophilic addition-elimination reaction on the C2 carbon of the benzimidazolium led to the formation of the intermediate state ($IS_1$) after overcoming the first transition state ($TS_1$). HB has a reaction free energy barrier ($\Delta G^{\ddagger}$) of 10.6 kcal $mol^{-1}$ for $TS_1$, which is considerably lower in energy compared to MeB (22.9 kcal $mol^{-1}$), and is similar to findings of Long and Pivovar. As $\Delta G^{\ddagger}$ is greatest for $TS_1$, the higher the energy for this rate-limiting step, the slower the ring-opening degradation. As such, MeB should have improved stability over that of HB, which is in good agreement with experimental observation. PhB is even more resistant to ring-opening degradation, consistent with the larger $\Delta G^{\ddagger}$ (24.2 kcal $mol^{-1}$).

Scheme 2. The two degradation pathways for benzimidazolium hydroxides (ring-opening and de-methylation).

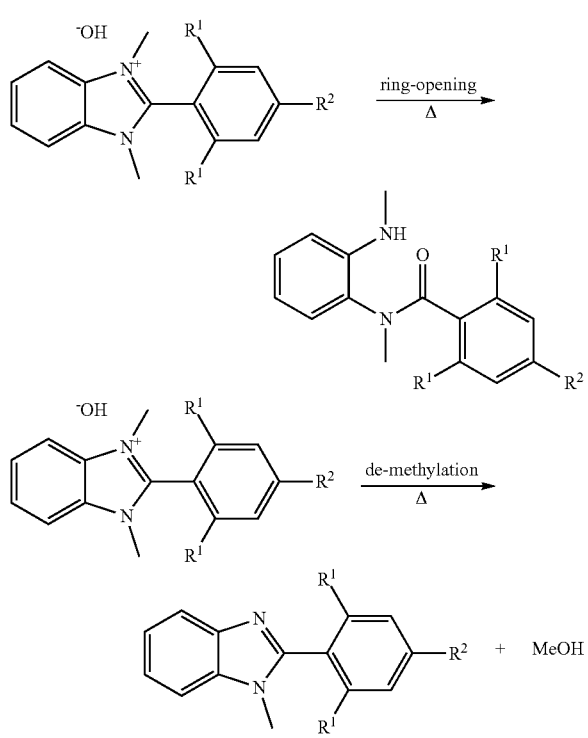

Figure 13:
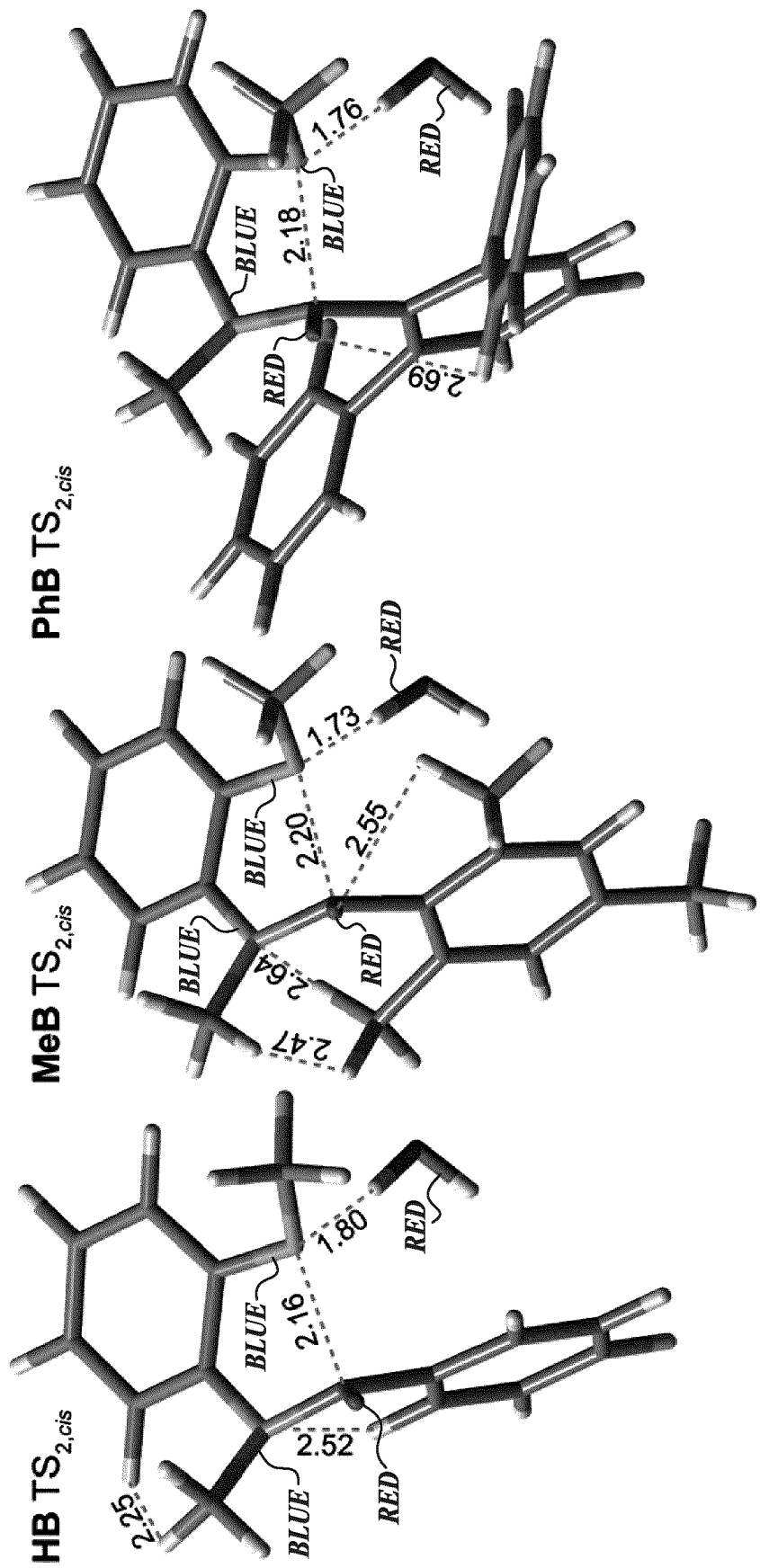
FIG. 13 shows the DFT structure of $TS_{2,cis}$ for HB, MeB, and PhB.
Figure 14:
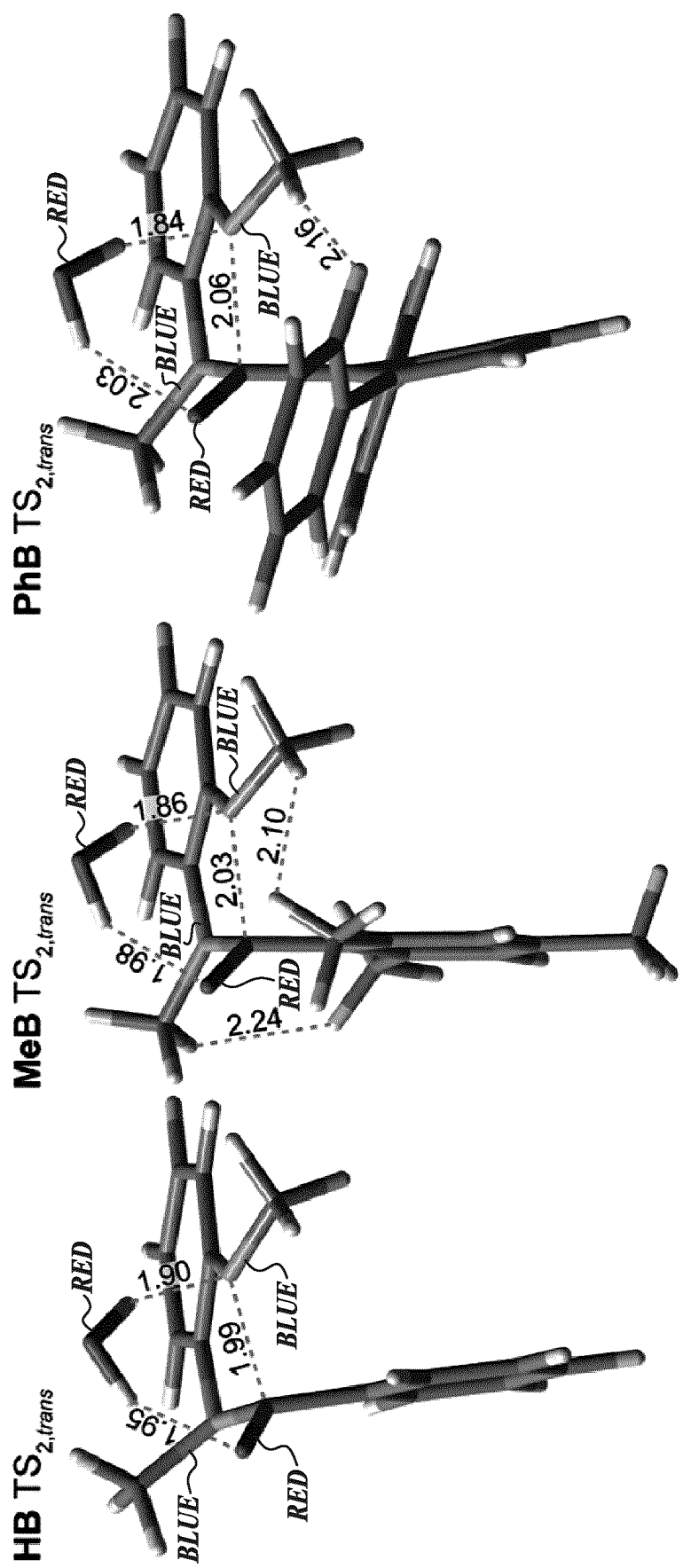
FIG. 14 shows the DFT structures of $TS_{2,trans}$ for HB, MeB, and PhB.
Figure 15:
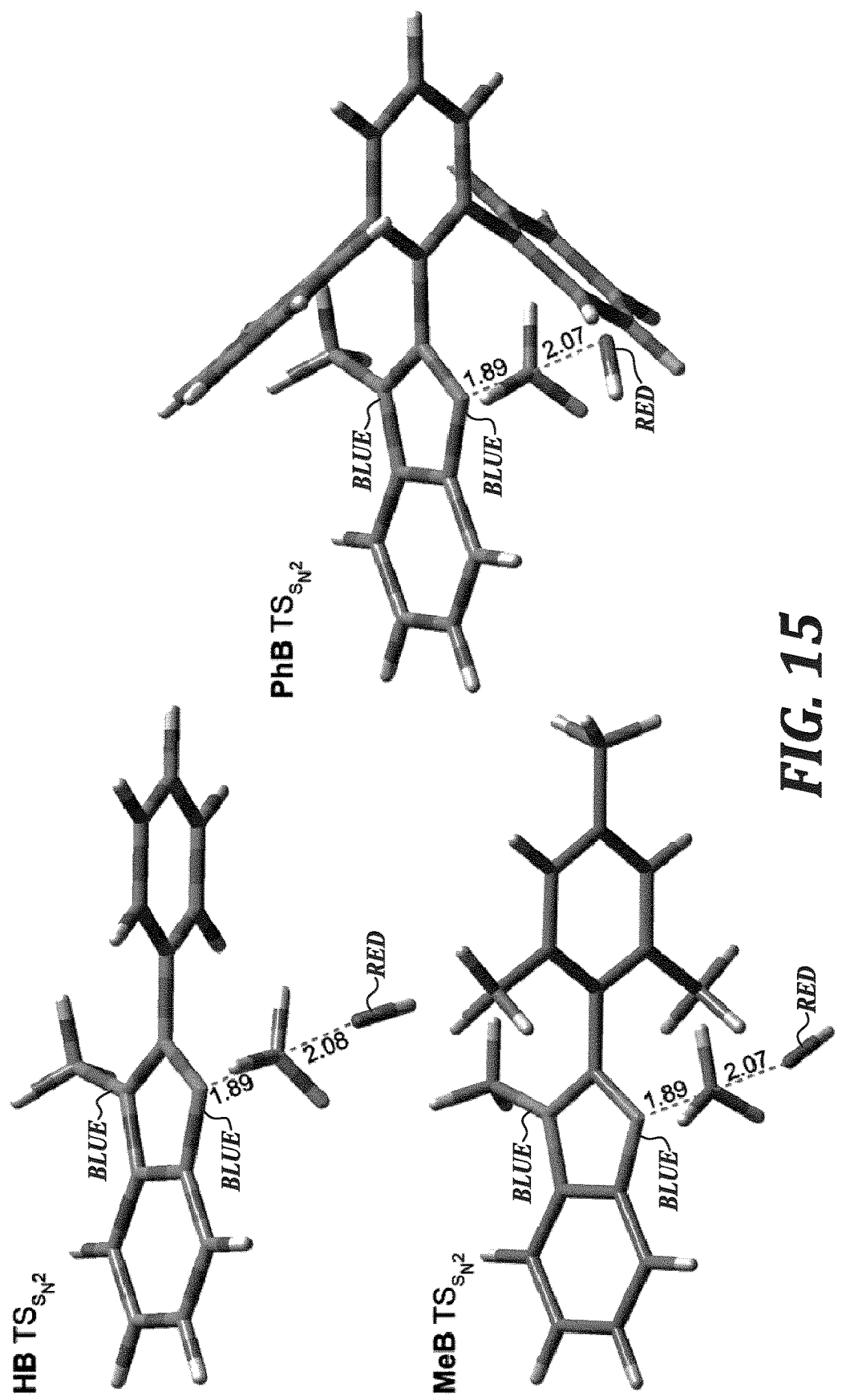
FIG. 15 shows the DFT structure of $TS_{SN2}$ for HB, MeB, and PhB.

The second transition state ($TS_2$) may proceed by one of two ways depending on the orientation of the two N-methyl groups ($TS_{2,trans}$ or $TS_{2,cis}$) and results in two different configurational isomers of the amide product (see FIGS. 13 and 14). $^1$H NMR spectra of degraded MeB revealed numerous amide products being formed, as only two alkyl peaks are expected for a single isomer configuration in the 3.0-2.0 ppm resonance region. Degraded products were also isolated and analyzed by mass spectrometry. Only the amide product was observed, with various amounts of deuterium exchange on the methyl groups. However, when the same process was performed on the isolated PhB degradation products, two products were observed). The ring-opened amide was present alongside the de-methylated product, which is the first observation of its kind for an alkali-degraded benzimidazolium hydroxide.

DFT calculations indicated that the activation energies of de-methylation differed only slightly between HB, MeB, and PhB ($\Delta G^{\ddagger}$ of $TS_{SN2}$ of 27.4, 26.9, and 27.3 kcal $mol^{-1}$, respectively). As $TS_1$ was generally significantly lower than $TS_{SN2}$, the de-methylation product was usually not observed. However, the substantial increase in the $\Delta G^{\ddagger}$ of $TS_1$ for PhB has decreased the energetic advantage of ring-opening degradation over that of de-methylation, with a difference of only 3.1 kcal $mol^{-1}$. While the effects of methanol were not considered in the DFT calculations, the estimated differences between the degradation rate and mechanism of individual model compounds were in good agreement between DFT and experiment.

In summary, through examination of benzimidazolium hydroxide model compounds, XRD, and DFT calculations, the effect on stability of four C2-protecting groups have been rationalized. A benzimidazolium was designed to be pendant on a poly(phenylene)-backbone in a manner that makes use of the sterically-protecting function of ortho-disubstituted phenylenes. Such polymers provided exceptional stability in alkaline solutions at 80° C. Moreover, a versatile synthetic route was presented that facilitates further investigations of numerous other C2-protecting groups.

Materials and Equipment

All chemicals were obtained from Sigma Aldrich and were ACS reagent grade unless otherwise stated. Mesitoic acid (98%) and 1,3-dibromobenzene (98%) were purchased from Combi-Blocks. Phenylboronic acid (98+%) and anhydrous dimethylsulfoxide (99.8+%) were purchased from Alfa Aesar. 4-chlorophenylboronic acid (98%) was purchased from Ark Pharm, Inc. Hydrochloric acid (37%, aq.), hexanes, potassium carbonate, diethyl ether, sodium chloride, and potassium chloride were purchased from ACP Chemicals Inc. Potassium hydroxide was purchased from Macron Fine Chemicals. Methanol, ethyl acetate, acetone, and methylene chloride (DCM) were purchased from Fisher Chemical. Tetrakis(triphenylphosphine)palladium(0) (99%) and bis(cyclooctadiene)nickel(0) (98+%) were purchased from Strem Chemicals Inc. Sodium hydroxide, magnesium sulfate, dimethyl sulfoxide (DMSO), and chloroform were purchased from BDH Chemicals. Ethanol was purchased from Commercial Alcohols. Basic aluminum oxide (Brockmann I, 50-200 μm, 60 Å) was purchased from Acros Organics. Eaton's reagent (7.7 wt % $P_2O_5$ in methanesulfonic acid) was prepared in advance by dissolution of $P_2O_5$ under argon atmosphere in methanesulfonic acid at 120° C. and then stored in glass at room temperature until needed. Dimethyl sulfoxide-$d_6$ (D, 99.9%) and methanol-$d_4$ (D, 99.8%, $CD_3OD$) were purchased from Cambridge Isotope Laboratories, Inc. Sodium deuteroxide (30 wt % in $D_2O$, 99 atom % D) and 1,1,2,2-tetrachloroethane-$d_2$ (D, 99.5%, $C_2D_2Cl_4$) were purchased from Sigma Aldrich. $^1$H NMR and $^{13}$C NMR spectra were obtained on a 500 MHz Bruker AVANCE III running IconNMR under TopSpin 2.1 and the residual solvent peaks for DMSO-$d_6$, $CD_3OD$, and $C_2D_2Cl_4$ were set to 2.50 ppm, 3.31 ppm, and 5.36 ppm for their $^1$H NMR spectra, respectively, and 39.52 ppm for the $^{13}$C NMR spectra in DMSO-$d_6$. Deionized water (DI water) was used from a Millipore Gradient Milli-Q® water purification system at 18.2 MS cm. Electrospray ionization mass spectrometry (ESI-MS) was performed using a Bruker micrOTOF in positive-mode.

Synthesis of 2,6-dibromobenzoic Acid (1)

2,6-dibromobenzoic acid was synthesized according to literature procedure. See, e.g., Varcoe, J. R. et al., *Chem. Mater.* 2007, 19, 2686-2693, incorporated herein in its entirety. More specifically, dry tetrahydrofuran (THF, 400 mL) in a 2-neck round-bottom flask under argon was cooled to 0° C. in an ice-water bath. n-Butyllithium (2.5 M in hexanes, 117 mL) was added followed by a slow addition of diisopropylamine (45 mL) at 0° C. to form lithium diisopropylamide (LDA). The mixture was stirred for 45 min and then cooled to −78° C. in a dry ice/acetone bath. While at this temperature, 1,3-dibromobenzene (50.0 g, 0.212 mol) was added drop-wise over 5 min and stirred for 1 h. Dry ice was then closed in a glass container and connected by syringe into the reaction mixture. After bubbling the mixture with the evolved gaseous $CO_2$ for 45 min, pieces of dry ice were added into the mixture. The mixture was allowed to slowly warm up to room temperature. Aqueous sodium hydroxide (0.5 M) and ethyl acetate (400 mL) were added until all of the solid was dissolved. The aqueous layer was washed with ethyl acetate and then acidified with concentrated hydrochloric acid until approximately pH=1. The precipitate was dissolved in fresh ethyl acetate, washed with brine, dried over $MgSO_4$, filtered, and the solvent was evaporated at 40° C. under vacuum. The oil was cooled to room temperature, resulting in crystallization. The solid was boiled in hexanes (2 L) for 1 h and then cooled to room temperature. The solid was collected, washed with hexanes, and dried under vacuum at 80° C., resulting in 1 (39.3 g, 66%) as an off-white powder. $^1$H NMR (500 MHz, DMSO-$d_6$, δ 7.70 (d, J=8.1 Hz, 2H), 7.29 (t, J=8.1 Hz, 1H). $^{13}$C NMR (125 MHz, DMSO-$d_6$, δ 166.87, 138.67, 131.87, 131.65.

Synthesis of
2-(2,6-dibromophenyl)-1H-benzimidazole (2)

In a 200 mL, 3-neck round-bottom flask with a $CaCl_2$ drying tube, stopper, and argon inlet was added 1 (17.00 g, 60.7 mmol), o-phenylenediamine (6.57 g, 60.8 mmol), and Eaton's reagent (136 mL). The mixture was heated to 120° C. under argon until fully dissolved. The mixture was then heated at 150° C. for 45 min. The mixture was poured into water (3.3 L) and neutralized to pH=7 using potassium hydroxide and potassium carbonate. The resulting precipitate was collected and washed with water. The solid was dried under vacuum at 90° C. to yield 2 (20.79 g, 97%) as an off-white powder. $^1$H NMR (500 MHz, DMSO-$d_6$, δ 12.87 (s, 1H), 7.84 (d, J=8.1 Hz, 2H), 7.69-7.56 (m, 2H), 7.44 (t, J=8.1 Hz, 1H), 7.30-7.20 (m, 2H). $^{13}$C NMR (125 MHz, DMSO-$d_6$, δ 149.71, 134.33, 132.95, 131.77, 124.51, 122.15. ESI-MS m/z calcd for $C_{13}H_9Br_2N_2^+$ [M$^+$-H]: 350.913, found 350.908.

Synthesis of
2-(2,6-dibromophenyl)-1-methyl-1H-benzimidazole (3)

In a 500 mL round-bottom flask was added powdered potassium hydroxide (6.18 g, 110 mmol) followed by DMSO (120 mL) and was vigorously stirred at room temperature for 30 min. A solution of 2 (20.00 g, 56.8 mmol) in DMSO (120 mL) was then added to the basic DMSO solution and stirred closed for 45 min at room temperature. Iodomethane (3.9 mL, 62.7 mmol) was then added and stirred for 45 min at room temperature. The mixture was poured into water (2.0 L) containing potassium hydroxide (10.0 g). Diethyl ether (500 mL) was added and the mixture stirred until fully dissolved. The organics were collected by decantation. The process was repeated by using additional diethyl ether (2×150 mL) and the combined organics were washed with water, brine, and water, dried over $MgSO_4$, filtered, and the solvent was evaporated. Drying under vacuum at room temperature resulted in 3 (18.20 g, 88%) as pale brown flakes. $^1$H NMR (500 MHz, DMSO-$d_6$, δ 7.89 (d, J=8.2 Hz, 2H), 7.69 (dd, J=23.2, 7.8 Hz, 2H), 7.49 (t, J=8.1 Hz, 1H), 7.32 (dt, J=28.6, 7.7 Hz, 1H), 3.58 (s, 3H). $^{13}$C NMR (125 MHz, DMSO-$d_6$, δ 150.80, 142.30, 134.88, 133.43, 132.64, 131.92, 124.77, 122.73, 122.01, 119.52, 110.66, 29.89. ESI-MS m/z calcd for $C_{14}H_{11}Br_2N_2^+$[M$^+$-H]: 364.928, found 364.924.

Synthesis of 2-([m-terphenyl]-2'-yl)-1-methyl-1H-benzimidazole (4)

In a 500 mL round-bottom flask was added 3 (8.00 g, 21.9 mmol), benzeneboronic acid (8.00 g, 65.6 mmol), 1,4-dioxane (240 mL), and 2 M $K_2CO_3$ $_{(aq.)}$ (80 mL). The mixture was bubbled with argon for 15 min and then tetrakis(triphenylphosphine)palladium(0) (106 mg, 0.4% mol per 3) was added. The mixture was heated 104° C. for 18 h and then poured into hot 33% ethanol (1.2 L, aq.). The resulting mixture was bubbled with air for 5 min until the solution became black and the mixture was cooled to room temperature while stirring. The resulting precipitate was collected and washed with water. The grey solid was dissolved in methylene chloride:ethyl acetate (1:1 vol.) and filtered through basic alumina by rinsing with the same solvent mixture. The filtrate was evaporated. The resulting solid was recrystallized from methanol and dried under vacuum at 80° C. to yield 4 (4.30 g, 55%) as colourless crystals with a faint yellow tint. $^1$H NMR (500 MHz, DMSO-$d_6$, δ 7.75 (t, J=7.7 Hz, 1H), 7.57 (d, J=7.8 Hz, 2H), 7.52-7.44 (m, 1H), 7.32-7.26 (m, 1H), 7.19-7.05 (m, 12H), 3.13 (s, 3H). $^{13}$C NMR (125 MHz, DMSO-$d_6$, δ 151.29, 143.02, 142.15, 140.11, 134.51, 130.32, 129.26, 128.37, 127.98, 127.33, 127.06, 121.80, 121.39, 118.94, 109.95, 29.75. ESI-MS m/z calcd for $C_{26}H_{21}N_2^+$ [M$^+$-H]: 361.170, found 361.172.

Synthesis of 2-([m-terphenyl]-2'-yl)-1,3-dimethyl-1H-benzimidazolium (PhB) Iodide In a 50 mL round-bottom flask was added 4 (3.00 g, 8.32 mmol) and methylene chloride (25 mL). Once fully dissolved, iodomethane (2.6 mL, 41.8 mmol) was added and the mixture was stirred closed at 30° C. for 17 h. The mixture was evaporated at 40° C. by dynamic vacuum and the resulting solid was briefly stirred in diethyl ether (50 mL). The solid was collected by vacuum filtration, washed with diethyl ether, and dried under vacuum at 80° C., yielding PhB (4.09 g, 98%) as an off-white powder. $^1$H NMR (500 MHz, DMSO-$d_6$, δ 8.08 (t, J=7.8 Hz, 1H), 7.92-7.87 (m, 2H), 7.85 (d, J=7.8 Hz, 2H), 7.70-7.62 (m, 2H), 7.36-7.25 (m, 6H), 7.20-7.13 (m, 4H), 3.53 (s, 6H). $^{13}$C NMR (125 MHz, DMSO-$d_6$, δ 149.25, 144.07, 137.90, 134.09, 130.64, 130.25, 128.97, 128.60, 127.96, 127.20, 117.30, 113.41, 32.42. ESI-MS m/z calcd for $C_{27}H_{23}N_2^+$ [M$^+$]: 375.186, found 375.187.

Synthesis of 2-(2,6-dibromophenyl)-1,3-dimethyl-1H-benzimidazolium (BrB) Iodide

In a 50 mL round-bottom flask was added 3 (4.00 g, 11.4 mmol) followed by methylene chloride (20 mL). Once fully dissolved, iodomethane (3.4 mL, 54.6 mmol) was added and the closed mixture was stirred 30° C. for 18 h. The solvent was evaporated at 44° C. by dynamic vacuum and diethyl ether (50 mL) was added. The solid was collected by vacuum filtration, washed with diethyl ether, and dried at 80° C. under vacuum, yielding BrB (5.21 g, 94%) as off-white powder. $^1$H NMR (500 MHz, DMSO-$d_6$, δ 8.29-8.20 (m, 2H), 8.14 (d, J=8.2 Hz, 2H), 7.92-7.84 (m, 2H), 7.79 (t, J=8.2 Hz, 1H), 3.98 (s, 6H). $^{13}$C NMR (125 MHz, DMSO-$d_6$, δ): 147.36, 136.96, 132.88, 131.14, 127.83, 124.64, 123.17, 114.16, 32.47. ESI-MS m/z calcd for $C_{15}H_{13}Br_2N_2^+$ [M$^+$]: 378.944, found 378.945.

Synthesis of 2-(4,4"-dichloro-[m-terphenyl]-2'-yl)-1-methyl-1H-benzimidazole (5)

In a 1 L round-bottom flask was added 3 (14.64 g, 40.0 mmol), 4-chlorophenylboronic acid (24.80 g, 159 mmol), 1,4-dioxane (366 mL), and 2 M $K_2CO_3$ $_{(aq.)}$ (132 mL). The mixture was bubbled with argon for 15 min and then tetrakis(triphenylphosphine)palladium(0) (0.46 g, 1% mol per 3) was added. The mixture was heated 104° C. for 19 h. As the solution was cooling to room temperature, the mixture was bubbled with air for 15 min until the solution colour darkened. The organics were collected by addition of ethyl acetate (600 mL) and washed with water, brine, and water. After drying the organic phase over magnesium sulfate, the solution was evaporated at 55° C. by rotary evaporation to yield an orange-coloured oil. The crude mixture was purified by flash chromatography on basic alumina using 1:2 vol ethyl acetate:hexanes. The collected solid was then washed with hexanes (400 mL) to yield off-white solid. This solid was recrystallized once in ethanol/water and three times in ethyl acetate/hexanes. Drying under vacuum at 100° C. yielded 5 (3.61 g, 21%) as a white powder. $^1$H NMR (500 MHz, DMSO-$d_6$, δ 7.77 (t, J=7.8 Hz, 1H), 7.59 (d, J=7.8 Hz, 2H), 7.51 (d, J=8.1 Hz, 1H), 7.36 (d, J=7.3 Hz, 1H), 7.22 (d, J=8.5 Hz, 4H), 7.18-7.09 (m, 6H), 3.17 (s, 3H). $^{13}$C NMR (125 MHz, DMSO-$d_6$, δ 150.82, 142.14, 141.88, 138.88, 134.61, 132.17, 130.67, 130.29, 129.68, 128.16, 127.27, 122.17, 121.75, 119.14, 110.31, 29.95. ESI-MS m/z calcd for $C_{26}H_{19}Cl_2N_2^+$[M$^+$-H]: 429.092, found 429.093.

Synthesis of poly(4,4"-[2'-(1-methyl-1H-benzimidazol-2-yl)-m-terphenylene]) (PPB)

To a 250 mL round-bottom flask was added 5 (1.9974 g, 4.65 mmol) and 2,2'-bipyridyl (1.7078 g, 10.9 mmol). The flask was capped with a septum. Using a needle through the septum, the flask was evacuated and refilled three times with argon. Bis(1,5-cyclooctadiene)nickel(0) (2.9414 g, 10.7 mmol) was then added by removing the septum and quickly recapping. The flask was evacuated and refilled three times with argon again. Anhydrous dimethylsulfoxide (130 mL) was then added and the mixture was heated at 80° C. while stirring for 19 h. The mixture was then poured into 1:1 vol $H_2O$:conc. HCl (1.0 L) and stirred for 30 min, causing the colour to change from black to white. The precipitate was collected by vacuum filtration over a glass frit and washed with water. The solid was stirred in a solution of potassium carbonate (10 g in 250 mL water) for 30 min. The solid was collected by vacuum filtration and washed with water followed by acetone. The solid was then stirred in acetone (200 mL) for 30 min. The solid was collected by vacuum filtration, washed with acetone, and dried at 100° C. under vacuum, yielding PPB (1.58 g, 95%) as a fluffy white solid. $^1$H NMR (500 MHz, $C_2D_2Cl_4$, δ 7.37-6.05 (m, 15H), 2.52 (s, 3H).

Synthesis of poly(4,4"-[2'-(1,3-dimethyl-1H-benzimidazolium-2-yl)-m-terphenylene]) (PPMB) Iodide In a 50 mL round-bottom flask was added PPB (1.00 g) followed by 1-methyl-2-pyrrolidinone (25 mL). The mixture was stirred and heated for 2 h at 80° C. until the polymer was fully dissolved. The mixture was then cooled to room temperature. Iodomethane (1.7 mL) was added and the mixture was stirred closed with a glass stopper at room temperature for 15 h. The solution was then poured slowly into stirring ethanol (600 mL). The resulting fibrous precipitate was collected and washed with ethanol. The solid was dried under vacuum at 80° C., resulting in PPMB (1.40 g, 100%) as a red, brittle, film-like solid. The $^1$H NMR spectrum was taken of the cast, water-washed, and 80° C. vacuum-dried membrane in its iodide form (see casting section for method). $^1$H NMR (500 MHz, DMSO-$d_6$, δ 8.20-7.98 (m, 1H), 7.96-7.76 (m, 4H), 7.70-7.61 (m, 2H), 7.60-7.36 (m, 4H), 7.32-7.08 (m, 4H), 3.57 (s, 6H).

Scheme S1. Synthetic route for the synthesis of MeB from mesitoic acid.

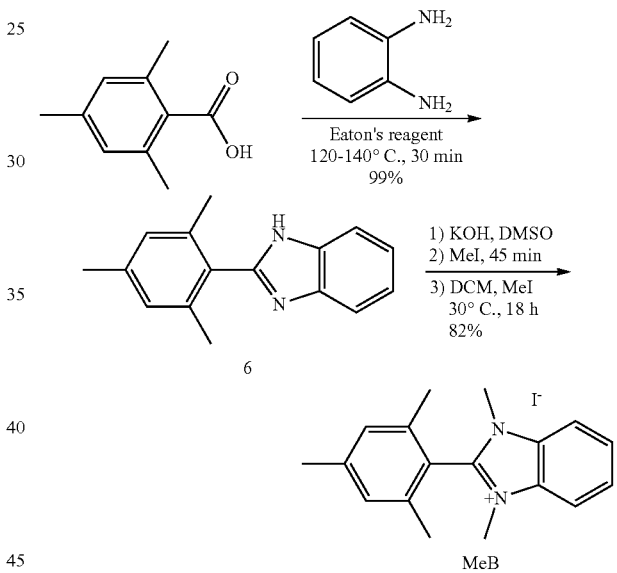

Synthesis of 2-mesityl-1H-benzimidazole (6)

In a 200 mL 3-neck round-bottom flask, attached with a $CaCl_2$ drying tube, glass stopper, and argon inlet, was added mesitoic acid (13.34 g, 81.2 mmol), o-phenylenediamine (8.79 g, 81.3 mmol), and Eaton's reagent (136 mL). Under argon flow, the mixture was heated to 120° C. for 15 min. The mixture was stirred for an additional 15 min at 140° C. and the mixture was then poured into distilled water (3.3 L). The mixture was neutralized to pH=7 by addition of potassium hydroxide and potassium carbonate. The resulting precipitate was collected by vacuum filtration, washed with water, and dried under vacuum at 90° C., yielding 6 (18.93 g, 98.6%) as a white powder. $^1$H NMR (500 MHz, DMSO-$d_6$, δ 12.51 (s, 1H) δ 7.61-7.51 (m, 2H), 7.23-7.16 (m, 2H), 6.99 (s, 2H), 2.31 (s, 3H), 2.06 (s, 6H). $^{13}$C NMR (125 MHz, DMSO-$d_6$, δ): 151.26, 138.36, 137.13, 128.89, 127.95, 121.50, 20.76, 19.70.

Synthesis of 2-mesityl-1,3-dimethyl-1H-benzimidazolium (MeB) Iodide

Powdered potassium hydroxide (2.24 g, 39.9 mmol) was added to a 250 mL round-bottom flask and vigorously stirred in DMSO (65 mL) for 30 min. A solution of 6 (5.00 g, 21.2 mmol) in DMSO (65 mL) was added to the basic DMSO solution and the mixture stirred for 45 min closed at room temperature. Iodomethane (1.4 mL, 22.5 mmol) was then added and the mixture stirred for 45 min. The mixture was then poured into a stirring solution of water (1.0 L) containing potassium hydroxide (5.0 g). Diethyl ether (300 mL) was then added and stirred until both layers were transparent. The organic layer was decanted and the same process was repeated with additional diethyl ether (2×150 mL). The combined organics were washed with water, brine, water, dried over magnesium sulfate, filtered, and evaporated at 44° C. under dynamic vacuum to yield a viscous pale yellow oil. Methylene chloride (25 mL) was added to the oil and stirred until fully dissolved. Iodomethane (6.0 mL, 96.4 mmol) was added and the mixture was stirred at 30° C. closed for 18 h. The solvent was evaporated at 44° C. using dynamic vacuum and diethyl ether (150 mL) was added. The solid was collected by vacuum filtration, washed with diethyl ether, and dried under vacuum at 80° C., yielding MeB (6.81 g, 82%) as an off-white powder. $^1$H NMR (500 MHz, DMSO-$d_6$, δ 8.19-8.09 (m, 2H), 7.82-7.75 (m, 2H), 7.26 (s, 2H), 3.83 (s, 6H), 2.40 (s, 3H), 2.05 (s, 6H). $^{13}$C NMR (125 MHz, DMSO-$d_6$, δ): 149.82, 143.01, 138.57, 131.59, 129.07, 126.74, 117.15, 113.84, 32.16, 20.95, 18.85. ESI-MS m/z calcd for $C_{18}H_{21}N_2^+$ [M$^+$]: 265.170, found 265.171.

Scheme 2. Synthetic route used to prepare HB from 2-phenylbenzimidazole.

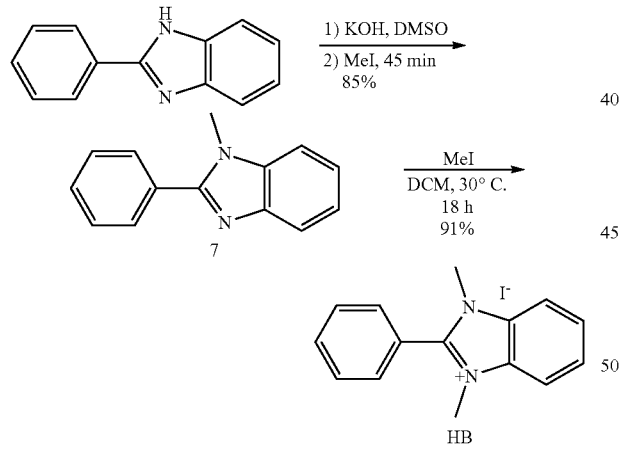

Synthesis of 2-phenyl-1-methyl-1H-benzimidazole (7)

Powdered potassium hydroxide (2.24 g, 39.9 mmol) was added to a 250 mL round-bottom flask and vigorously stirred in DMSO (65 mL) for 30 min. A solution of 2-phenylbenzimidazole (4.11 g, 21.2 mmol) in DMSO (65 mL) was added to the basic DMSO solution and the mixture stirred for 45 min closed at room temperature. Iodomethane (1.4 mL, 22.5 mmol) was then added and the mixture stirred for 45 min. The mixture was then poured into a stirring solution of water (1.0 L) containing potassium hydroxide (5.0 g). Diethyl ether (300 mL) was then added and stirred until both layers were transparent. The organic layer was decanted and the same process was repeated with additional diethyl ether (2×200 mL). The combined organics were washed with water, brine, water, dried over magnesium sulfate, filtered, and evaporated at 44° C. under dynamic vacuum to yield 7 (3.74 g, 85%) as a pale brown powder. $^1$H NMR (500 MHz, DMSO-$d_6$, δ 7.86 (dd, J=7.8, 1.7 Hz, 2H), 7.69 (d, J=7.9 Hz, 1H), 7.64-7.52 (m, 4H), 7.33-7.22 (m, 2H), 3.88 (s, 3H). $^{13}$C NMR (125 MHz, DMSO-$d_6$, δ): 152.98, 142.47, 136.57, 130.15, 129.60, 129.28, 128.63, 122.32, 121.90, 118.98, 110.53, 31.64.

Synthesis of 2-phenyl-1,3-dimethyl-1H-benzimidazolium (HB) Iodide

Methylene chloride (20 mL) was added to 7 (3.00 g, 14.4 mmol) in a 50 mL round-bottom flask and stirred until fully dissolved. Iodomethane (2.7 mL, 43.4 mmol) was added and the mixture was stirred at 30° C. closed for 17 h. The solvent was evaporated at 45° C. using dynamic vacuum and diethyl ether was added. The solid was collected by vacuum filtration, washed with diethyl ether, and dried under vacuum at 40° C., yielding HB (4.59 g, 91%) as an off-white powder. $^1$H NMR (500 MHz, DMSO-$d_6$, δ 8.15 (dd, J=6.2, 3.1 Hz, 2H), 7.93 (d, J=7.0 Hz, 2H), 7.88-7.73 (m, 5H), 3.91 (s, 6H). $^{13}$C NMR (125 MHz, DMSO-$d_6$, δ): 150.29, 132.91, 131.68, 130.76, 129.42, 126.61, 120.96, 113.39, 32.85. ESI-MS m/z calcd for $C_{15}H_{15}N_2^+$ [M$^+$]: 223.123, found 223.124.

Intrinsic Viscosity

Four separate solutions of PPB at various concentrations in NMP (2-5 mg mL$^{-1}$) were first prepared by gently heating the mixtures until fully dissolved. The solutions were then filtered through 0.45 m PTFE syringe filters. The viscosity (η) of each solution was then measured using a temperature-controlled (25.0° C.) RheoSense, Inc. μVisc viscometer equipped with a 0.2-100 cP sensor. The settings were set to "AUTO" except for the shear rate, which was set to 5000 s$^{-1}$. Prior to each measurement, the solution was allowed to thermally equilibrate for 5 min. Four measurements were taken for each concentration and averaged. The specific viscosity ($\eta_{sp}$) and relative viscosity ($\eta_{rel}$) were then calculated for the measured concentrations using Equation S1 and Equation S2, respectively.

$$\eta_{sp} = \frac{\eta}{\eta_{solvent}} \quad \text{S1}$$

$$\eta_{rel} = \frac{\eta}{\eta_{solvent}} - 1 \quad \text{S2}$$

where $\eta_{solvent}$ is the viscosity measured for the pure solvent.

Figure 3:
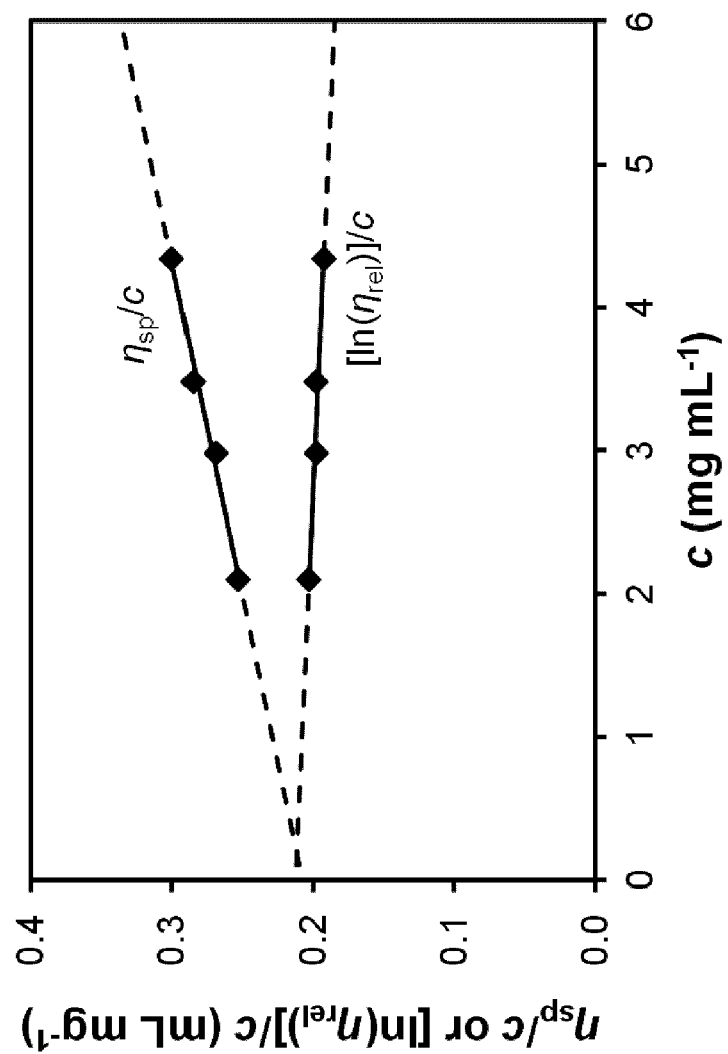
FIG. 3 is a Huggins-Kraemer plot of PPB in NMP calculated from the measured viscosities at 25.0° C. for various concentrations (c).
Figure 4:
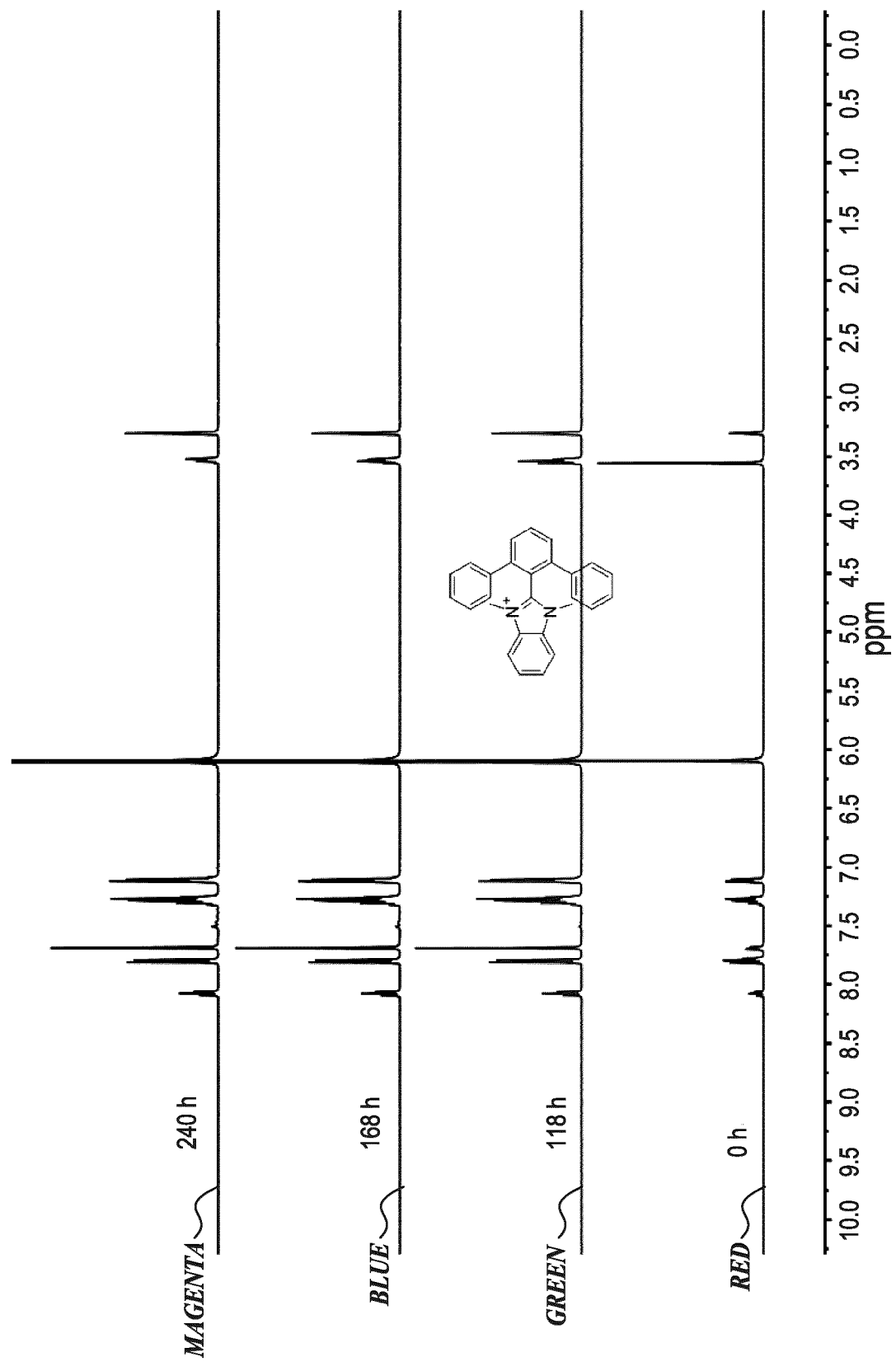
FIG. 4 shows $^1H$ NMR spectra of PhB (0.02 M) in 3 M $NaOD/CD_3OD/D_2O$ after heating at 80° C. for the specified duration.
Figure 5:
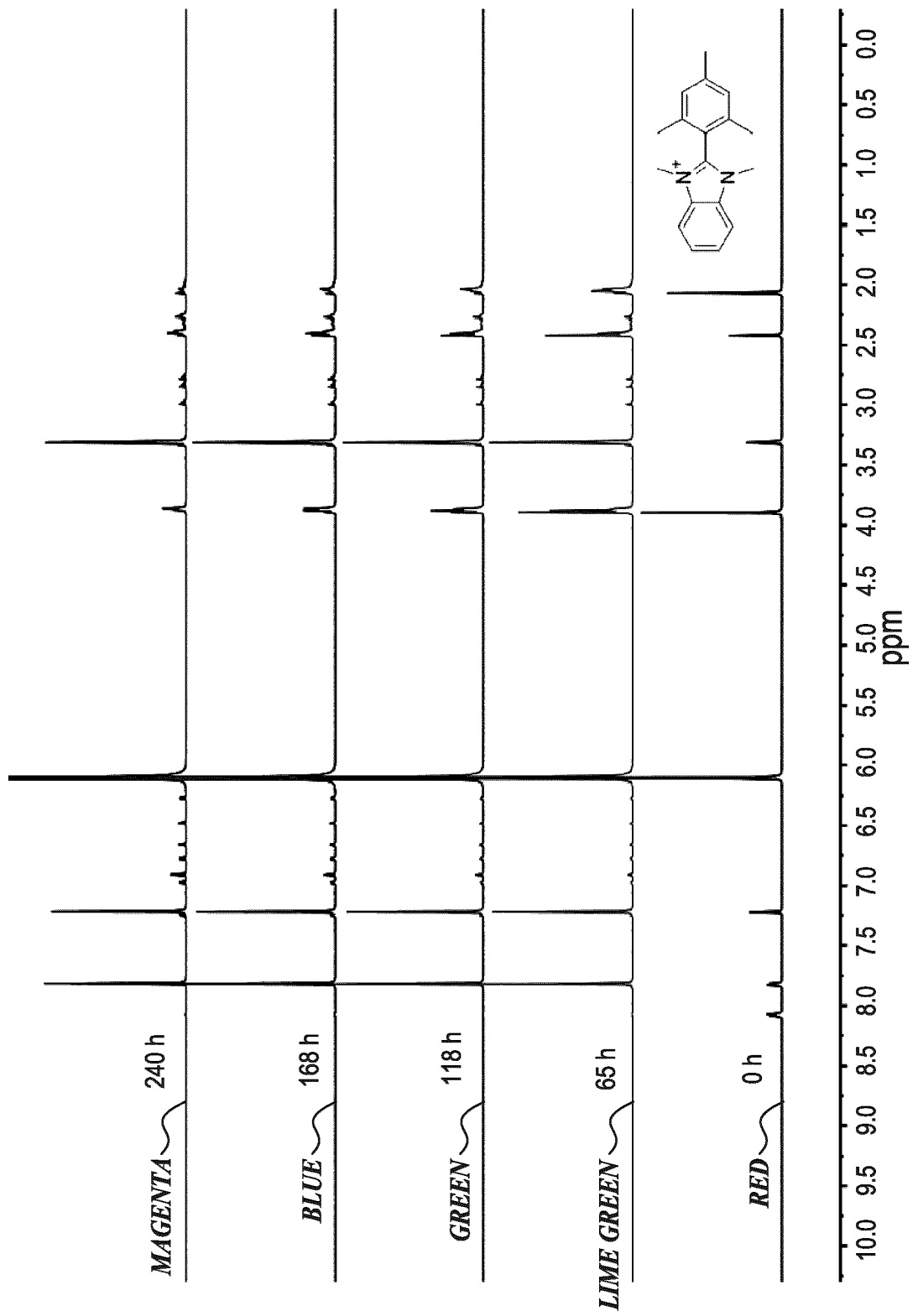
FIG. 5 shows $^1H$ NMR spectra of MeB (0.02 M) in 3 M $NaOD/CD_3OD/D_2O$ after heating at 80° C. for the specified duration.

A plot of the Huggins ($\eta_{sp}/c$) and Kraemer ([ln($\eta_{rel}$)]/c) parameters versus concentration (c) is shown in FIG. 3. The average of the two y-intercepts, calculated from the extrapolation of the Huggins-Kraemer linear regressions, represents the intrinsic viscosity. From FIG. 3, the intrinsic viscosity of PPB was calculated to be 0.210 mL mg$^{-1}$ or, equivalently, 2.10 dL g$^{-1}$.

Membrane Preparation Method

PPMB in its iodide form (1.5 wt % in DMSO) was evenly spread in a flat Petri dish and dried at 86° C. in air for 24 h. DI water was added to the dish and the membrane was peeled off of the glass. The membrane was soaked in DI water for 24 h, 1 M NaCl for 48 h, and DI water for 24 h at room temperature. The membrane was then dried at 80° C. under vacuum. This chloride-exchanged membrane was then recast as 1.5 wt % PPMB in DMSO as previously described. This chloride-cast membrane was then peeled off the glass using DI water and soaked in DI water for at least 24 h before use in the subsequent experiments.

Water Uptake

Pieces of a PPMB membrane in chloride form were soaked in 1 M KOH for 48 h followed by multiple fresh exchanges of DI water over 48 h. After removing the surface water with a kimwipe, the wet (hydrated) mass was measured ($m_{wet}$). The pieces were soaked in 1 M NaCl (with one fresh exchange in between) for 4 days followed by several DI water exchanges for 24 h. The membrane pieces were then dried under vacuum at 50° C. and weighed to yield the dry mass ($m_{dry}$). The water uptake (WU) was then calculated from the average of four samples and the standard deviation was used as the uncertainty using Equation S3.

$$WU = \frac{m_{wet} - m_{dry}}{m_{dry}} \quad\quad S3$$

Ionic Conductivity

Membrane pieces of PPMB (chloride-form) were soaked in 1 M KOH for 48 h at room temperature followed by soaking in DI water with multiple fresh exchanges over an additional 48 h at room temperature under ambient atmosphere. A piece of this wet hydroxide/carbonate membrane (~0.5×1.0×0.005 cm$^3$) was placed across two platinum plates, all of which were sandwiched between two PTFE blocks for good contact. While wet (fully hydrated) and at 22° C., the in-plane resistance and impedance were measured over a frequency range of 10$^7$-10$^2$ Hz using a Solartron SI 1260 gain/phase analyzer. The ionic resistance (R) was determined from a best-fit regression of Randles circuit to the data and the ionic conductivity ($\sigma$) was calculated using Equation S4. The average of four different samples (each measured four times) was calculated and the standard deviation was used as the uncertainty.

$$\sigma(mS\,cm^{-1}) = 10000 \frac{L}{R \times T \times W} \quad\quad S4$$

where R is the ionic resistance ($\Omega$), L is the distance between the two platinum electrodes (mm), T is the thickness of the membrane (mm), and W is the width of the membrane (mm).

Degradation Tests of the Model Compounds

Each model compound in its iodide form (HB, BrB, MeB, and PhB) was dissolved in 3 M NaOD/CD$_3$OD/D$_2$O (prepared by diluting 2.05 g of 30 wt % NaOD (in D$_2$O) with CD$_3$OD to 5.0 mL) inside PTFE containers, such that the final concentration of each model compound in the solution was 0.02 M. Once fully dissolved, ~0.6 mL of the solution was removed and analyzed by $^1$H NMR spectroscopy ("0 h" spectrum). The tightly-closed PTFE containers were then heated in an oven at 80° C. and samples were removed at certain points in time for $^1$H NMR spectroscopic analysis. The spectra, which were all baseline-corrected using the "Full Auto (Polynomial Fit)" function found in MestReNova 9.0.1, are shown in FIGS. 4-7.

The percent remaining of PhB and MeB over time (from the $^1$H NMR spectra) was calculated using Equation S5. This formula involves the integration of an aryl peak that does not overlap with any other peaks, including any that would appear from degradation products, relative to the total aryl region, which includes all degradation aryl protons. For PhB and MeB, only two aryl protons are deuterium-exchanged under these degradation conditions, which are the 4- and 7-position protons of the benzimidazolium, and are completely exchanged for deuterium by 68 h. For example, the total number of aryl protons of MeB at 0 h is 6H but decreases to 4H for the 68-240 h spectra.

$$\text{Remaining Starting Material}(\%) = 100\left(\frac{\frac{n_t * x_t}{y_t}}{\frac{n_0 * n_0}{y_0}}\right) \quad\quad S5$$

where $n_t$ is the number of expected protons in the aromatic region (17 and 6 for PhB and MeB, respectively, at 0 h and 15 and 4 for 68 h and higher, respectively), $x_t$ is the integration value for the 8.13-8.02 ppm region relative to the integration of the total aryl region, $y_t$, at 8.31-6.26 ppm for PhB (for MeB, $x_t$ and $y_t$ are the integration regions of 7.87-7.75 ppm relative to 8.20-6.23 ppm, respectively), and $n_0$, $x_0$, and $y_0$ represent the 0 h values.

Figure 8:
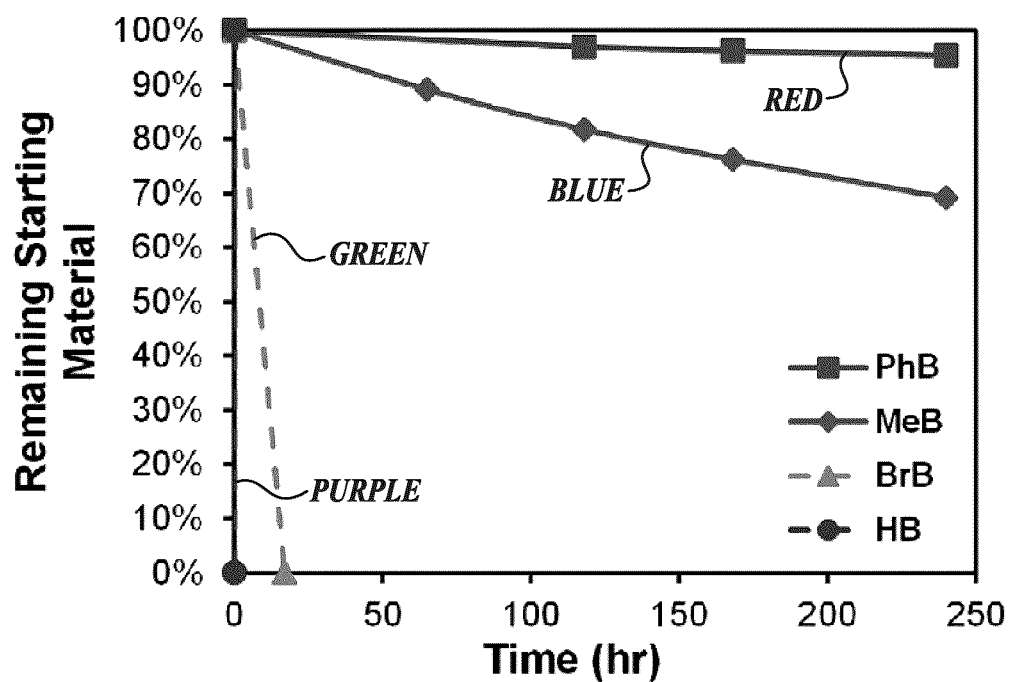
FIG. 8 is a graph showing a measurement of remaining starting material over time for the dissolved model compounds (0.02 M) in 3 M $NaOD/CD_3OD/D_2O$ at 80° C. as determined by $^1H$ NMR spectroscopy.

The calculated remaining starting material for the model compounds over time is plotted in FIG. 8.

Identification of Model Compound Degradation Products

After the previously mentioned 3M NaOD/CD$_3$OD/D$_2$O, 80° C., 240 h degradation test of MeB and PhB, each solution was cooled to room temperature. The organic degradation products were then isolated using the following method (PhB as the example):

The PhB mixture was acidified with dilute, aqueous hydrochloric acid until the pH was neutral, resulting in precipitate. Diethyl ether was added to fully dissolve the precipitate and the organic layer was washed with water three times, dried over MgSO$_4$, filtered, and evaporated at 40° C. using a dynamic vacuum. The resulting residue was then analyzed by mass spectrometry.

Degradation Test of the Polymer

Three membrane pieces of PPMB (chloride-form) were initially soaked in 1 M KOH for 48 h at room temperature followed by soaking in DI water with multiple fresh exchanges over an additional 48 h at room temperature under ambient atmosphere. One of the membrane pieces was then soaked in 1 M NaCl for 48 h (with one fresh exchange in between) and DI water for 24 h (multiple fresh exchanges). After drying at 50° C. under vacuum, the piece was dissolved in DMSO-d$_6$ and analyzed by $^1$H NMR spectroscopy (represents the "initial" spectrum). The second and third membrane pieces (~25 mg each) were immersed in either 30 mL of aqueous 1 M or 2 M KOH in closed FEP containers inside an 80° C. oven for 168 h. These membrane pieces were then transferred into 1 M NaCl or KCl and soaked for 72 h (with one fresh exchange in between) followed by soaking in DI water for 48 h (with multiple fresh exchanges). These membrane pieces were then dried under an argon stream and part of each sample was dissolved in DMSO-d$_6$ and analyzed by $^1$H NMR spectroscopy ("168 h" spectra). The $^1$H NMR spectra, which were baseline-corrected using the "Full Auto (Polynomial Fit)" function found in MestReNova 9.0.1, are shown in FIG. 9.

The extent of degradation was calculated using Equation S5, where $x_t$ represents the integration of the 8.56-8.01 ppm region relative to the aryl region, $y_t$, of 8.56-5.88 ppm, and n is equal to 1 for all three spectra (as there is no deuterium present); $x_0$ and $y_0$ represent the same region integrations but for the "initial" spectrum only. For FIG. 9, the amount of remaining starting material for "1 M KOH, 168 h" is 98.3%, meaning 1.7% degradation is observed, whereas for "2 M KOH, 168 h" it is 94.7%, meaning 5.3% degradation is observed.

APEX2 Suite followed by structural refinements using ShelXle. The collected crystal data is tabulated in Table S1 and CCDC 1439721-1439724 contains the supplementary crystallographic data for this paper. The data can be obtained free of charge from The Cambridge Crystallographic Data Centre via www.ccdc.cam.ac.uk/getstructures. The structural figures were prepared using Mercury.

TABLE S1

Crystal structure data for each of the four model compounds that were crystallized in their iodide forms.

| | HB | BrB | MeB | PhB•H$_2$O |
|---|---|---|---|---|
| crystallization method | by slow cooling of a solution of HB in EtOH from reflux to RT in air | by slow evaporation of BrB in H$_2$O under ambient conditions | by slow evaporation of MeB in H$_2$O under ambient conditions | by slow evaporation of PhB in EtOAc/EtOH under ambient conditions |
| colour and shape | colourless block | colourless needle | colourless sheet | colourless block |
| refined formula | C$_{15}$H$_{15}$I$_1$N$_2$ | C$_{15}$H$_{13}$Br$_2$I$_1$N$_2$ | C$_{18}$H$_{21}$I$_1$N$_2$ | C$_{27}$H$_{23}$I$_1$N$_2$•H$_2$O |
| formula weight (g mol$^{-1}$) | 350.203 | 507.995 | 392.284 | 520.414 |
| crystal dimensions (mm$^3$) | 0.211 × 0.288 × 0.388 | 0.077 × 0.117 × 0.224 | 0.092 × 0.148 × 0.354 | 0.523 × 0.254 × 0.176 |
| radiation | Cu Kα | Mo Kα | Cu Kα | Mo Kα |
| wavelength (Å) | 1.54178 | 0.71073 | 1.54178 | 0.71073 |
| crystal system | monoclinic | monoclinic | orthorhombic | monoclinic |
| space group | P2$_1$/c | P2$_1$/c | Pbca | P2$_1$/n |
| a (Å) | 11.7933(3) | 11.5893(4) | 9.72290(10) | 12.6275(6) |
| b (Å) | 8.2391(2) | 19.6291(7) | 11.59830(10) | 13.5185(7) |
| c (Å) | 15.6325(3) | 15.4023(5) | 32.4106(4) | 14.1586(7) |
| α (°) | 90 | 90 | 90 | 90 |
| β (°) | 111.2550(10) | 106.7010(10) | 90 | 99.1810(10) |
| γ (°) | 90 | 90 | 90 | 90 |
| V (Å$^3$) | 1415.63 | 3356.02 | 3654.92 | 2385.98 |
| Z | 4 | 8 | 8 | 4 |
| T (K) | 296(2) | 296(2) | 299(2) | 296(2) |
| ρ$_{calcd}$ (g cm$^{-3}$) | 1.643 | 2.011 | 1.426 | 1.449 |
| μ (mm$^{-1}$) | 17.633 | 6.663 | 13.719 | 1.362 |
| 2θ$_{max}$ (°) | 145.16 | 64.356 | 133.174 | 53.110 |
| observed reflections[a] | 2636 | 6677 | 2854 | 3973 |
| R$_{int}$ | 0.0516 | 0.0337 | 0.0428 | 0.0208 |
| R[a] | 0.0412 | 0.0367 | 0.0381 | 0.0309 |
| wR[a] | 0.1047 | 0.0650 | 0.1063 | 0.0733 |
| goodness of fit | 1.042 | 1.000 | 1.041 | 1.111 |
| CCDC # | 1439721 | 1439723 | 1439722 | 1439724 |

[a]for $I_o > 2\sigma(I_o)$.

Mechanical Strength

A PPMB (iodide form) membrane, that was previously washed with water and dried under vacuum at 80° C., was cut into a barbell shape using an ASTM D638-4 cutter. The 40 μm thick sample was pulled apart at both ends at a rate of 5.00 mm min$^1$ on a single column system (Instron® 3344 Series) until broken under ambient conditions (21° C., 42% RH). The measured force at each point was then used to calculate the stress and is shown in FIG. 10. The Young's modulus was calculated from the slope of a linear regression in the 0.5%-2.0% strain region.

Single Crystal X-Ray Diffraction

The four different model compounds (HB, BrB, MeB, and PhB) were crystallized in their iodide forms (see Table S1 for the crystallization method). The single-crystal x-ray crystallography was performed on a Bruker SMART APEX II system with an APEX II CCD detector and a tunable graphite crystal monochromator. The detector was placed at 5.0 cm from each crystal and measured under ambient conditions. The data was collected and processed using the Density Functional Theory Electronic structure calculations for the model compounds as well as the degradation of HB, MeB, and PhB were performed using Gaussian G09, B3LYP density functional theory (DFT), and Polarizable Continuum Model (PCM) using the in G09 integrated Integral Equation Formalism (IEFPCM) with water as solvent ($\varepsilon$=78.36). Pre-optimization was performed using 6-31G(d) basis set. Final calculations were done using 6-311++G(2d,2p) basis set, tight convergence criteria and no symmetry. Structures of reagents, intermediate structures (IS) and products (P) were optimized to energy minimum; transition states (TS) were optimized using the G09 implemented Berny algorithm, having one imaginary frequency. Intermediates of HB were confirmed by calculating the intrinsic reaction coordinates. Frequency analysis was performed using a temperature of 298.15 K. Reaction free energy ($\Delta G$) and reaction free energy barrier ($\Delta G^\ddagger$) are given with respect to the sum of the reagent free energy: benzimidazolium cation+2 OH$^-$ for the addition-elimination reaction and benzimidazolium cation+ OH⁻ for the $S_N2$ reaction. All structure geometries can be found in FIG. 11-15.

TABLE S2

Calculated $\Delta G$ and $\Delta G^\ddagger$ for cations at 25° C. and 1 atm. The reaction limiting barrier is marked bold.

| | | Ring-opening degradation pathway | | | | | De-methylation degradation pathway | |
|---|---|---|---|---|---|---|---|---|
| Name | Reagents [kcal/mol] | $TS_1$ [kcal/mol] | $IS_1$ [kcal/mol] | $IS_2$ [kcal/mol] | $TS_{2,cis}$ [kcal/mol] | $TS_{2,trans}$ [kcal/mol] | $TS_{SN2}$ [kcal/mol] | $P_{SN2}$ [kcal/mol] |
| HB | 0.0 | 10.6 | −4.6 | −16.7 | 0.3 | −1.5 | 27.4 | −29.1 |
| MeB | 0.0 | 22.9 | 7.8 | −2.5 | 13.5 | 13.0 | 26.9 | −28.0 |
| PhB | 0.0 | 24.2 | 7.3 | −3.9 | 14.1 | 13.3 | 27.3 | −29.4 |

While illustrative embodiments have been illustrated and described, it will be appreciated that various changes can be made therein without departing from the spirit and scope of the disclosure.

The embodiments of the disclosure in which an exclusive property or privilege is claimed are defined as follows:

1. A polymer comprising repeating units of Formula (II-A) and (II-B)

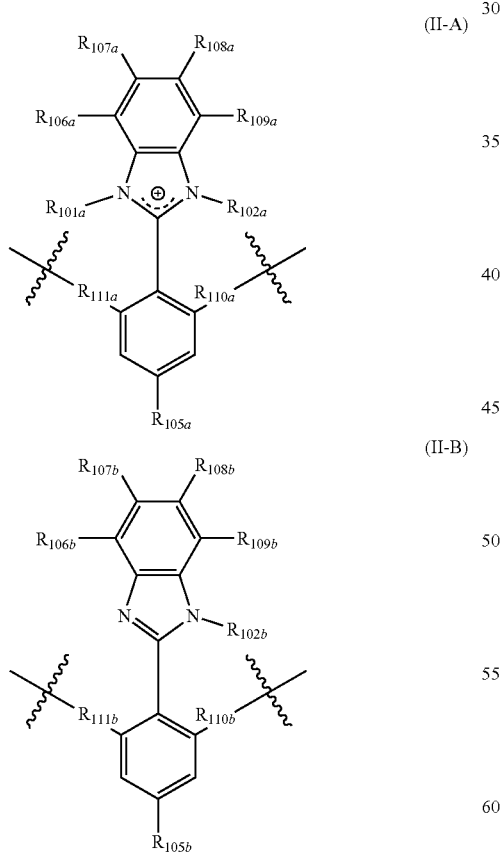

wherein:

$R_{101a}$, $R_{102a}$, and $R_{102b}$ are each independently selected from alkyl, perfluoroalkyl, heteroalkyl, aryl, aralkyl, and heteroaryl;

$R_{111a}$, $R_{110a}$, $R_{111b}$, and $R_{110b}$ are each independently selected from alkylene, perfluoroalkylene, heteroalkylene, arylene, aralkylene, heteroarylene, wherein said alkylene, perfluoroalkylene, heteroalkylene, arylene, aralkylene, or heteroarylene is each optionally substituted with 1, 2, 3, or 4 substituents independently selected from alkyl and halo;

$R_{105a}$ and $R_{105b}$ are each independently selected from hydrogen, alkyl, perfluoroalkyl, heteroalkyl, aryl, aralkyl, and heteroaryl;

$R_{106a}$, $R_{107a}$, $R_{108a}$, $R_{109a}$, $R_{106b}$, $R_{107b}$, $R_{108b}$, and $R_{109b}$ are each independently selected from hydrogen, alkyl, perfluoroalkyl, heteroalkyl, aryl, aralkyl, and heteroaryl, wherein the polymer comprises comprising r mole percentage repeating units of Formula (II-A), and s mole percentage repeating units of Formula (II-B), and r is from 1 mole percent to 100 mole percent, s is from 0 mole percent to 99 mole percent, and r+s=100%.

2. The polymer of claim 1, wherein $R_{101a}$, $R_{102a}$, and $R_{102b}$ are each independently selected from alkyl, perfluoroalkyl, and heteroalkyl.

3. The polymer of claim 1, wherein $R_{101a}$, $R_{102a}$, and $R_{102b}$ are each methyl.

4. The polymer of claim 1, wherein $R_{111a}$, $R_{110a}$, $R_{111b}$, and $R_{110b}$ are each phenylene, wherein said phenylene is optionally substituted with 1, 2, 3, or 4 substituents independently selected from alkyl and halo.

5. The polymer of claim 1, wherein $R_{105a}$ and $R_{105b}$ are each independently selected from hydrogen, alkyl, perfluoroalkyl, heteroalkyl, aryl, and heteroaryl.

6. The polymer of claim 1, wherein $R_{105a}$ and $R_{105b}$ are each independently selected from hydrogen and methyl.

7. The polymer of claim 1, wherein $R_{106a}$, $R_{107a}$, $R_{108a}$, and $R_{109a}$, $R_{106b}$, $R_{107b}$, $R_{108b}$, and $R_{109b}$ are each hydrogen.

8. The polymer of claim 1, further comprising one or more anions X⁻ selected from iodide, bromide, chloride, fluoride, triiodide, hydroxide, carbonate, bicarbonate, cyanide, acetate, nitrate, sulfate, phosphate, triflate, tosylate, tetrakis (3,5-bis(trifluoromethyl)phenyl)borate, bis(trifluoromethane)sulfonamide, and any combination thereof, wherein the one or more anions X⁻ counterbalance the positive charges in the polymer.

9. An ionic membrane comprising the polymer of claim 1.

10. The polymer of claim 1, wherein the polymer is incorporated into a catalyst layer of a fuel cell, of an electrolyzer, or of other electrochemical devices.

* * * * *

UNITED STATES PATENT AND TRADEMARK OFFICE
CERTIFICATE OF CORRECTION

Page 1 of 1

PATENT NO. : 10,800,874 B2
APPLICATION NO. : 16/068654
DATED : October 13, 2020
INVENTOR(S) : S. Holdcroft et al.

It is certified that error appears in the above-identified patent and that said Letters Patent is hereby corrected as shown below:

In the Claims

| Column | Line |  |
|--------|------|--|
| 36 | 31 | "comprises comprising r" to -- comprises r -- |

Signed and Sealed this
Twenty-fifth Day of May, 2021

Drew Hirshfeld
*Performing the Functions and Duties of the
Under Secretary of Commerce for Intellectual Property and
Director of the United States Patent and Trademark Office*